United States Patent
Zhai et al.

(10) Patent No.: US 11,905,300 B2
(45) Date of Patent: Feb. 20, 2024

(54) COMPOUND, MATERIAL FOR AN ORGANIC ELECTROLUMINESCENT DEVICE AND APPLICATION THEREOF

(71) Applicants: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

(72) Inventors: Lu Zhai, Shanghai (CN); Wei Gao, Shanghai (CN); Wenpeng Dai, Shanghai (CN); Lei Zhang, Shanghai (CN); Quan Ran, Shanghai (CN)

(73) Assignees: WUHAN TIANMA MICRO-ELECTRONICS CO., LTD., Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 371 days.

(21) Appl. No.: 17/386,558

(22) Filed: Jul. 28, 2021

(65) Prior Publication Data
US 2021/0355142 A1 Nov. 18, 2021

(30) Foreign Application Priority Data
Apr. 23, 2021 (CN) .......................... 202110444015.7

(51) Int. Cl.
*H01L 29/08* (2006.01)
*C07D 519/00* (2006.01)
(Continued)

(52) U.S. Cl.
CPC ......... *C07D 519/00* (2013.01); *H10K 85/624* (2023.02); *H10K 85/626* (2023.02);
(Continued)

(58) Field of Classification Search
CPC .. C07D 519/00; H10K 85/624; H10K 85/636; H10K 85/633; H10K 85/626;
(Continued)

(56) References Cited

FOREIGN PATENT DOCUMENTS

| CN | 103022376 A | 4/2013 |
|---|---|---|
| CN | 108727271 A | 11/2018 |

(Continued)

*Primary Examiner* — Niki H Nguyen
(74) *Attorney, Agent, or Firm* — KILPATRICK TOWNSEND & STOCKTON LLP

(57) ABSTRACT

The present disclosure relates to a compound, a material for an organic electroluminescent device and an application thereof. The compound provided by the present disclosure has a relatively high refractive index and can effectively improve the light extraction efficiency and the external quantum efficiency of an organic electroluminescent device when used in the organic electroluminescent device especially as a material for the capping layer. The compound has a relatively high refractive index in the region of visible light (400-750 nm), which is conducive to improving the light-emitting efficiency. The compound has a relatively large extinction coefficient in the ultraviolet region (less than 400 nm), which is conducive to absorbing harmful light and protecting eyesight and has a relatively small extinction coefficient in the region of blue light (400-450 nm) and hardly absorbs blue light, which is conducive to improve the light-emitting efficiency.

17 Claims, 1 Drawing Sheet

(51) Int. Cl.
*H10K 85/60* (2023.01)
*H10K 50/11* (2023.01)

(52) U.S. Cl.
CPC ......... *H10K 85/633* (2023.02); *H10K 85/636* (2023.02); *H10K 85/6572* (2023.02); *H10K 85/6574* (2023.02); *H10K 50/11* (2023.02)

(58) Field of Classification Search
CPC ............... H10K 85/6572; H10K 50/11; H10K 2101/10; H10K 85/342; H10K 85/615; H10K 85/654; H10K 85/631; H10K 85/657; H10K 50/15; H10K 85/40; H10K 50/16; H10K 85/622; H10K 85/6576; H10K 85/346; H10K 50/12; H10K 85/30; H10K 85/322; H10K 50/171; H10K 50/125; H10K 85/341; H10K 50/115; H10K 59/40; H10K 71/00; H10K 2102/103; H10K 50/155; H10K 85/381; H10K 50/165; H10K 85/60; H10K 2102/351; H10K 85/361; H10K 85/649; H10K 50/86; H10K 2101/27; H10K 85/111; H10K 59/122; H10K 30/865; H10K 85/652; H10K 50/80; H10K 50/865; H10K 71/15; H10K 50/828; H10K 59/32; H10K 71/164; H10K 2102/301; H10K 50/818; H10K 59/125; H10K 85/141; H10K 2102/3023; H10K 30/81

See application file for complete search history.

(56) References Cited

FOREIGN PATENT DOCUMENTS

| CN | 111732530 A | * 10/2020 | ........... C07C 211/61 |
|---|---|---|---|
| CN | 111892587 A | 11/2020 | |
| CN | 112125873 A | * 12/2020 | ........... C07C 211/61 |
| CN | 112745330 A | 5/2021 | |

* cited by examiner

COMPOUND, MATERIAL FOR AN ORGANIC ELECTROLUMINESCENT DEVICE AND APPLICATION THEREOF

CROSS-REFERENCE TO RELATED APPLICATION(S)

This application claims priority to Chinese Patent Application No. 202110444015.7 filed on Apr. 23, 2021, the disclosure of which is incorporated herein by reference in its entirety.

FIELD

The present disclosure relates to the field of organic electroluminescence and in particular, to a compound, a material for an organic electroluminescent device and an application thereof.

BACKGROUND

After decades of development, organic electroluminescence (such as organic light-emitting diode, OLED) has gained considerable progress. The OLED has an internal quantum efficiency of approximately 100% and an external quantum efficiency of only about 20%. Most light is confined inside a light-emitting device due to factors such as a loss of a substrate mode, a surface plasmon loss and a waveguide effect, resulting in a loss of a large amount of energy.

In a top emitting device, an organic capping layer (CPL) is deposited through evaporation on a translucent metal electrode Al so that an optical interference distance is adjusted, the reflection of external light is suppressed, and the extinction caused by the movement of surface plasmon is suppressed, improving light extraction efficiency and light-emitting efficiency.

High requirements are imposed on the performance of a material for CPL: no absorption within the wavelength range (400 nm to 700 nm) of visible light, a high refractive index (generally, n>2.1), a low extinction coefficient (k≤0.00) within the wavelength range of 400 nm to 600 nm, a high glass transition temperature, a high molecular thermal stability, and an ability to be deposited through evaporation without thermal decomposition.

Materials for CPL in the related art still have many problems, for example, (1) the refractive index is generally below 1.9 and cannot meet the requirement for high refractive index; (2) in the case where the refractive index meets the requirement, the materials have relatively strong absorption or a relatively large extinction coefficient in the region of visible light; (3) amine derivatives with a particular structure and a high refractive index and the use of materials that have particular parameters have improved the light extraction efficiency, while the problems of light-emitting efficiency and chromaticity are still to be solved especially for blue light-emitting elements; (4) to increase the density of molecules and achieve high thermal stability, a molecular structure is designed to be large and loose so that molecules cannot be tightly packed, resulting in too many molecular gel holes during evaporation and incomplete coverage; (5) a simple design of an electron-type capping layer material to achieve the effects of electron transmission and light extraction saves a preparation cost of the device to a certain extent so that multiple effects are achieved, while the design is not conducive to light extraction and improves the light-emitting efficiency only slightly and the problem of chromaticity is not solved.

Therefore, more kinds of CPL materials with higher performance are to be developed in the art.

SUMMARY

In view of defects in the related art, a first object of the present disclosure is to provide a compound, and in particular an organic electroluminescent material, specifically a material for a capping layer. The compound has a relatively high refractive index and can effectively improve the external quantum efficiency (EQE) of an organic photoelectric device when used as a material for the capping layer. Meanwhile, the compound has a relatively small extinction coefficient in the region of blue light (400-450 nm) and hardly absorbs blue light, improving the light-emitting efficiency.

Embodiments are described below.

The present disclosure provides a compound, which has a structure represented by Formula (1):

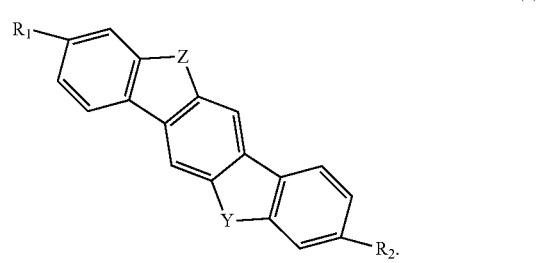

Formula (1)

In Formula (1), $R_1$ and $R_2$ are each independently selected from a benzoxazole-containing group and a benzothiazole-containing group.

In Formula (1), Y and Z are each independently selected from any one of O, S, $NR_3$ and $CR_4R_5$, where $R_3$ is selected from substituted or unsubstituted C6-C60 aryl and substituted or unsubstituted C3-C60 heteroaryl, and $R_4$ and $R_5$ are each independently selected from any one of a hydrogen atom, substituted or unsubstituted C6-C60 aryl and substituted or unsubstituted C3-C60 heteroaryl.

Substituted groups in $R_3$, $R_4$ and $R_5$ are each independently selected from any one or a combination of at least two of protium, deuterium, tritium, cyano, halogen, C1-C10 alkyl, C1-C10 haloalkyl, C1-C10 alkoxy, C6-C60 aryl and C3-C60 heteroaryl.

A second object of the present disclosure is to provide a material for an organic electroluminescent device. The material for an organic electroluminescent device includes any one or a combination of at least two of the compound as described for the first object.

A third object of the present disclosure is to provide an organic electroluminescent device. The organic electroluminescent device includes a first electrode layer, an organic function layer and a second electrode layer which are stacked in sequence.

The organic function layer includes the material as described for the second object.

A fourth object of the present disclosure is to provide an organic electroluminescent device. The organic electroluminescent device includes a first capping layer, a first electrode layer, an organic function layer and a second electrode layer which are stacked in sequence.

The first capping layer includes the material as described for the second object.

A fifth object of the present disclosure is to provide a display panel. The display panel includes the organic electroluminescent device as described for the fourth object.

A sixth object of the present disclosure is to provide a display device. The display device includes the display panel as described for the fifth object.

Compared with the related art, the present disclosure has beneficial effects described below.

The compound provided by the present disclosure has a relatively high refractive index in the region of visible light (400-750 nm), which is conducive to improving the light-emitting efficiency. The compound has a relatively large extinction coefficient in the ultraviolet region (less than 400 nm), which is conducive to absorbing harmful light and protecting eyesight. And the compound has a relatively small extinction coefficient in the region of blue light (400-450 nm) and hardly absorbs blue light, which is conducive to improve the light-emitting efficiency.

Figure 1:
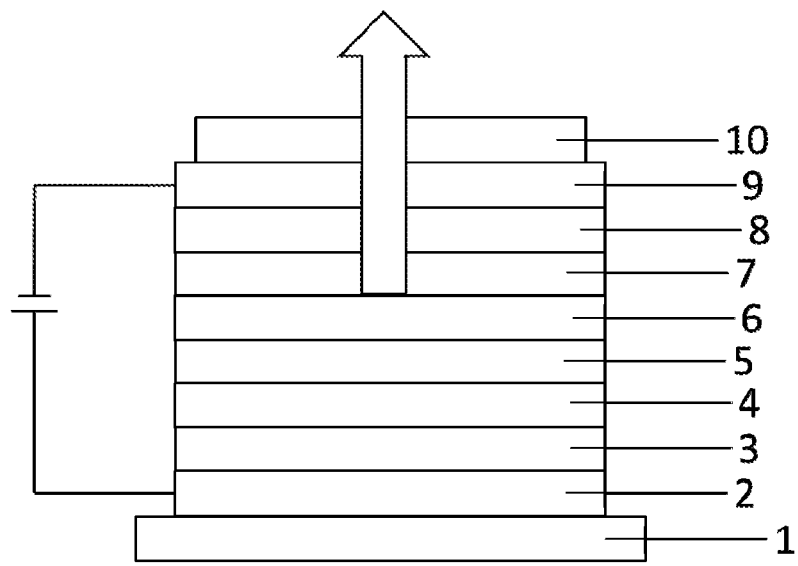
FIG. 1 is a structure diagram of an organic electroluminescent device according to an embodiment of the present disclosure.

REFERENCE LIST 1 substrate
2 anode
3 hole injection layer
4 first hole transport layer
5 second hole transport layer
6 light-emitting layer
7 first electron transport layer
8 second electron transport layer
9 cathode
10 first capping layer
11 second capping layer

DETAILED DESCRIPTION

For a better understanding of the present disclosure, examples of the present disclosure are listed below. The examples described herein are used for a better understanding of the present disclosure and not to be construed as specific limitations to the present disclosure.

A first object of the present disclosure is to provide a compound. The compound has a structure represented by Formula (1):

Formula (1)

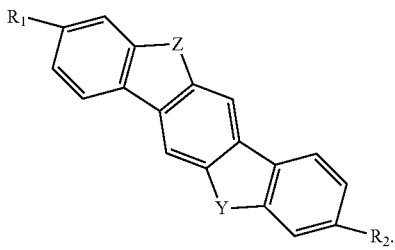

In Formula (1), $R_1$ and $R_2$ are each independently selected from a benzoxazole-containing group and a benzothiazole-containing group.

In Formula (1), Y and Z are each independently selected from any one of O, S, $NR_3$ and $CR_4R_5$, where $R_3$ is selected from substituted or unsubstituted C6-C60 (for example, C8, C10, C12, C14, C16, C18, C20, C22, C24, C26, C28, C30, C32, C34, C36, C38, C40, C42, C44, C46, C48, C50, C52, C54, C56, C58 or the like) aryl and substituted or unsubstituted C3-C60 (for example, C4, C5, C6, C7, C8, C10, C12, C14, C16, C18, C20, C22, C24, C26, C28, C30, C32, C34, C36, C38, C40, C42, C44, C46, C48, C50, C52, C54, C56, C58 or the like) heteroaryl, and $R_4$ and $R_5$ are each independently selected from any one of a hydrogen atom, substituted or unsubstituted C6-C60 (for example, C8, C10, C12, C14, C16, C18, C20, C22, C24, C26, C28, C30, C32, C34, C36, C38, C40, C42, C44, C46, C48, C50, C52, C54, C56, C58 or the like) aryl and substituted or unsubstituted C3-C60 (for example, C4, C5, C6, C7, C8, C10, C12, C14, C16, C18, C20, C22, C24, C26, C28, C30, C32, C34, C36, C38, C40, C42, C44, C46, C48, C50, C52, C54, C56, C58 or the like) heteroaryl.

Substituted groups in $R_3$, $R_4$ and $R_5$ are each independently selected from any one or a combination of at least two of protium, deuterium, tritium, cyano, halogen, C1-C10 (for example, C2, C3, C4, C5, C6, C7, C8, C9 or the like) alkyl, C1-C10 (for example, C2, C3, C4, C5, C6, C7, C8, C9 or the like) haloalkyl, C1-C10 (for example, C2, C3, C4, C5, C6, C7, C8, C9 or the like) alkoxy, C6-C60 (for example, C8, C10, C12, C14, C16, C18, C20, C22, C24, C26, C28, C30, C32, C34, C36, C38, C40, C42, C44, C46, C48, C50, C52, C54, C56, C58 or the like) aryl and C3-C60 (for example, C4, C5, C6, C7, C8, C10, C12, C14, C16, C18, C20, C22, C24, C26, C28, C30, C32, C34, C36, C38, C40, C42, C44, C46, C48, C50, C52, C54, C56, C58 or the like) heteroaryl.

The present disclosure provides a new type of compound with

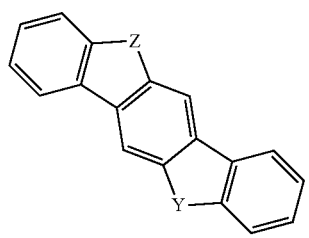

as a parent core and containing a benzoxazole-containing group or a benzothiazole-containing group as substituents on benzene rings at two ends of the parent core. The compound has a relatively high refractive index in the region of visible light and can effectively improve the light extraction efficiency and external quantum efficiency (EQE) of an organic electroluminescent device when used in the organic electroluminescent device especially as a material for the capping layer. Moreover, the compound of the present disclosure has a relatively large extinction coefficient in an ultraviolet region (less than 400 nm), which is conducive to absorbing harmful light and protecting eyesight and has a relatively small extinction coefficient in the region of blue light (400-450 nm) and hardly absorbs blue light, which is conducive to improve the light-emitting efficiency.

In an embodiment, the compound has any one of the following structures:

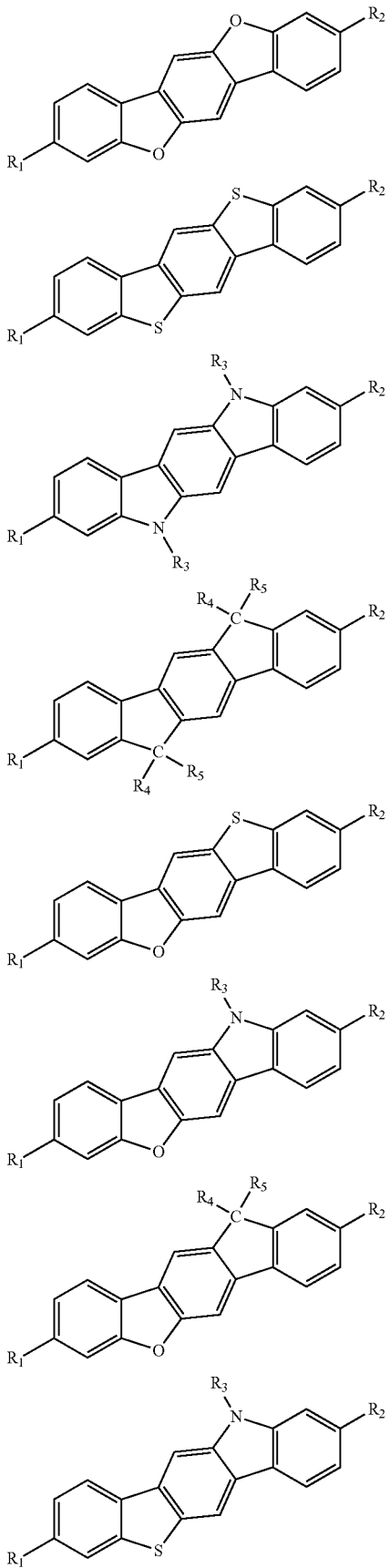

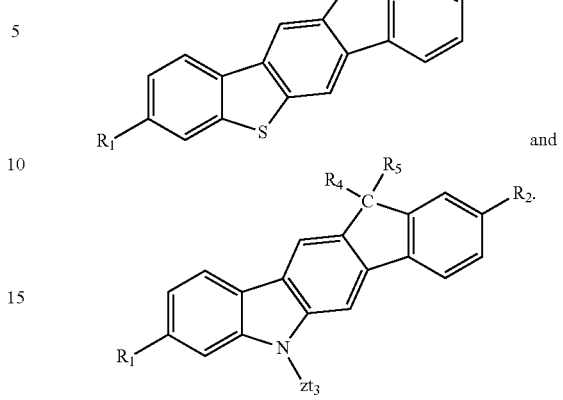

$R_1$, $R_2$, $R_3$, $R_4$ and $R_5$ each have the same selection ranges as the above.

In an embodiment, $R_1$ and $R_2$ each independently have a structure represented by Formula (2) or Formula (3):

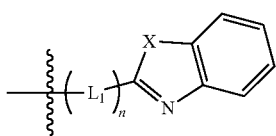

Formula (2)

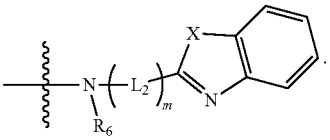

Formula (3)

The squiggle represents a linkage site of the group.

In the above Formulae, n and m are each independently 0 or 1, $L_1$ and $L_2$ are each independently selected from substituted or unsubstituted C6-C60 arylene, $R_6$ is selected from substituted or unsubstituted C6-C60 aryl and substituted or unsubstituted C3-C60 heteroaryl, and X is selected from O and S.

Substituted groups in $L_1$, $L_2$ and $R_6$ are each independently selected from any one or a combination of at least two of protium, deuterium, tritium, cyano, halogen, C1-C10 alkyl, C1-C10 haloalkyl, C1-C10 alkoxy, C6-C60 aryl and C3-C60 heteroaryl.

In an embodiment, at least one of $R_1$ and $R_2$ has the structure represented by Formula (3).

In an embodiment of the present disclosure, benzoxazole or benzothiazole is linked via an arylamino group to at least one end of the parent core. Such a structure increases the degree of conjugation and obtains a relatively high refractive index.

In an embodiment, $R_1$ and $R_2$ each have the structure represented by Formula (3).

In the present disclosure, further preferably, benzoxazole or benzothiazole at the two ends of the parent core are both linked via an arylamino group. Compared with the structure of arylamine on a single end, such a structure increases a conjugation length and thus can further improve the refractive index and reduce the difficulty of synthesis.

In an embodiment, n and m are each 1.

In the present disclosure, preferably, a linking group $L_1$ or $L_2$ is present between benzoxazole/benzothiazole and the parent core/a N atom. Such a structure increases the degree of conjugation and obtains a higher refractive index.

In an embodiment, $L_1$ and $L_2$ are each independently selected from substituted or unsubstituted phenylene.

In an embodiment, $R_6$ is selected from any one of or a group formed through the linkage of at least two of substituted or unsubstituted phenyl, substituted or unsubstituted biphenyl, substituted or unsubstituted terphenyl, substituted or unsubstituted quaterphenyl, substituted or unsubstituted naphthyl, substituted or unsubstituted phenanthryl, substituted or unsubstituted fluorenyl, substituted or unsubstituted carbazolyl, substituted or unsubstituted dibenzofuryl, substituted or unsubstituted dibenzothienyl, substituted or unsubstituted pyrimidinyl, substituted or unsubstituted triazinyl, substituted or unsubstituted indolocarbazolyl, substituted or unsubstituted indolobenzofuryl, substituted or unsubstituted indolobenzothienyl, substituted or unsubstituted benzofuranpyrimidinyl, substituted or unsubstituted benzothiophenepyrimidinyl, substituted or unsubstituted anthryl, substituted or unsubstituted pyrenyl, substituted or unsubstituted pyrrolyl, substituted or unsubstituted furyl, substituted or unsubstituted thienyl, substituted or unsubstituted indolyl, substituted or unsubstituted indenocarbazolyl, substituted or unsubstituted pyridyl, substituted or unsubstituted pyrazinyl and substituted or unsubstituted pyridazinyl.

In an embodiment, $R_6$ is selected from

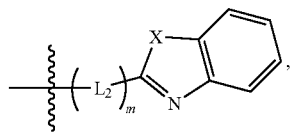

where $L_2$, m and X each have the same ranges as defined in Formula (3).

The squiggle represents a linkage site of the group.

In an embodiment, the compound has any one of the following structures represented by M1 to M45:

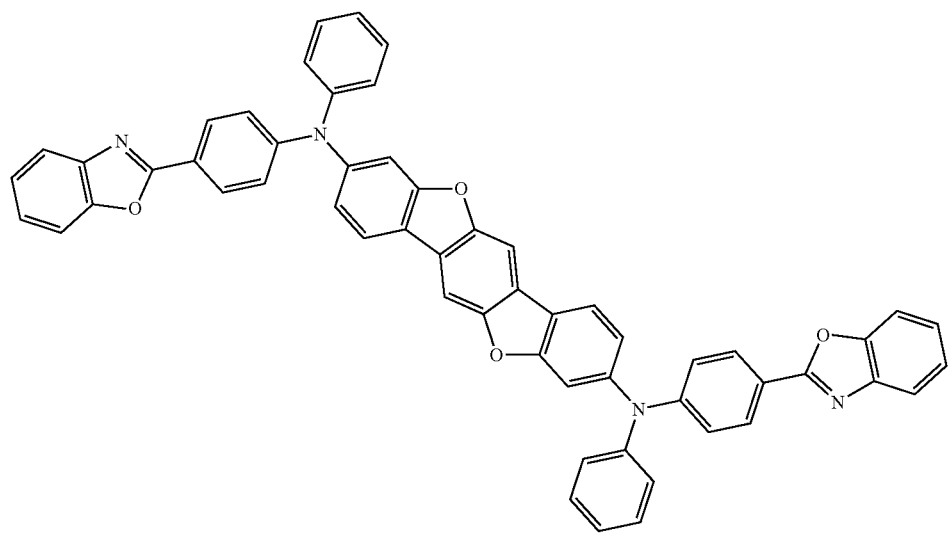

M1

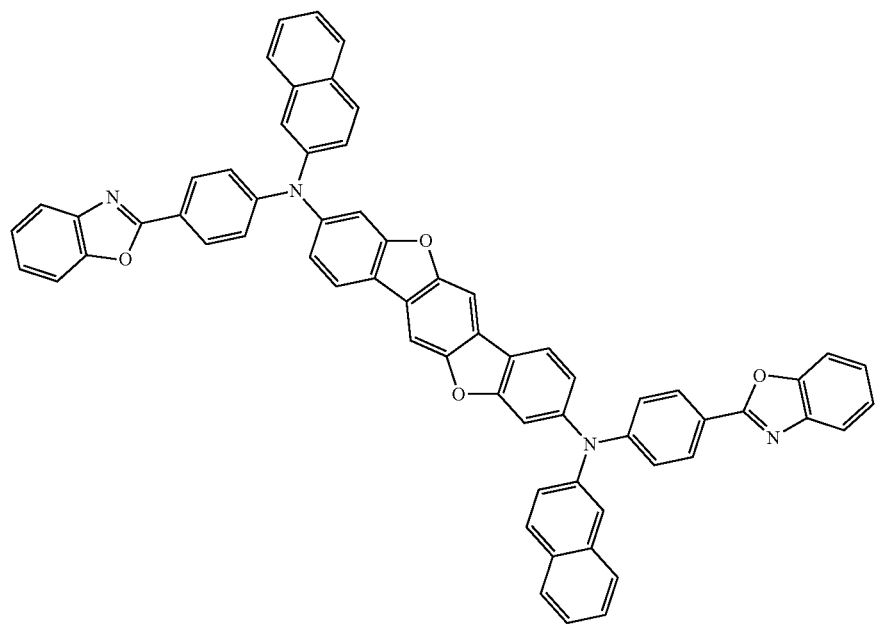

M2

-continued
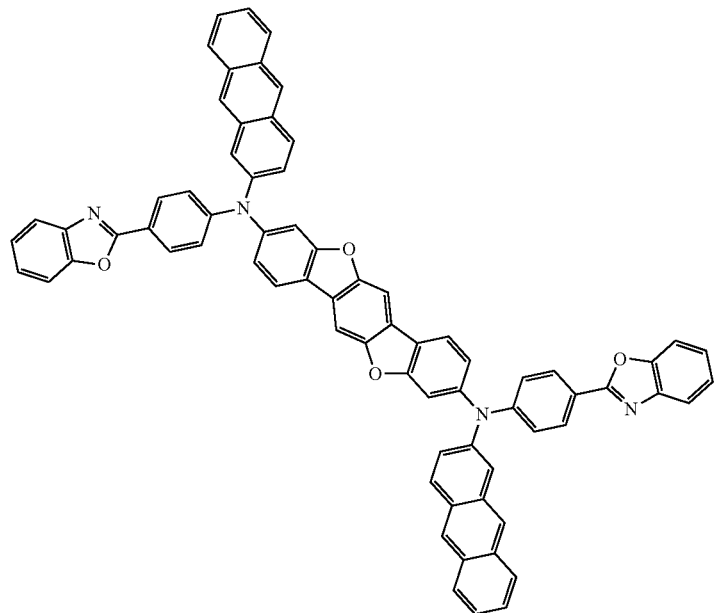
M3
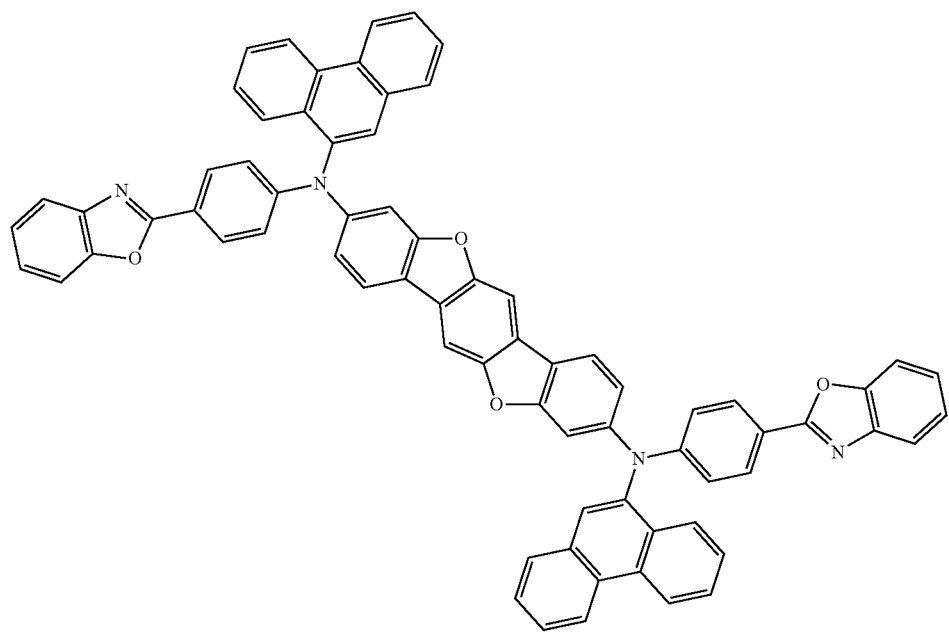
M4

M5
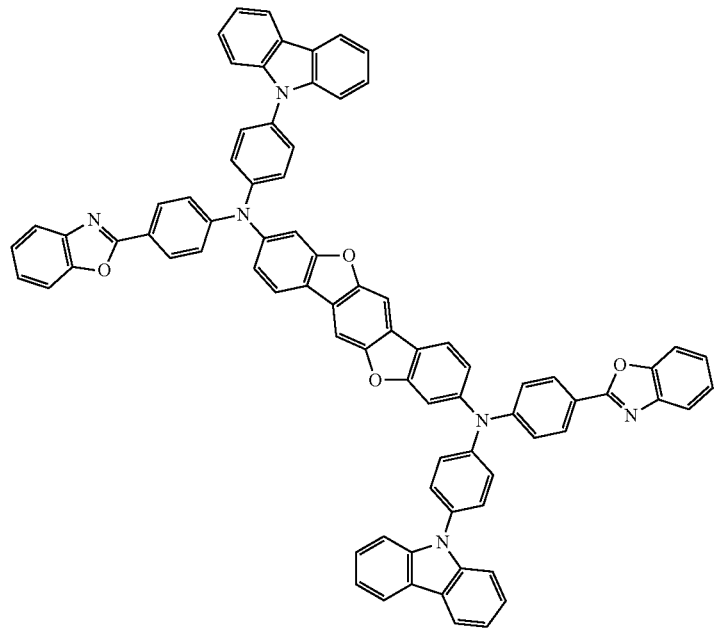
M6
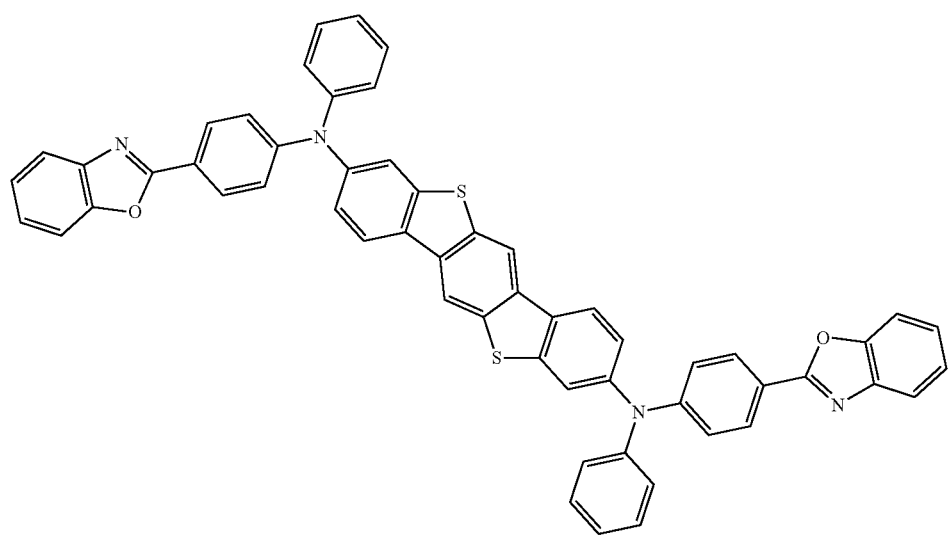

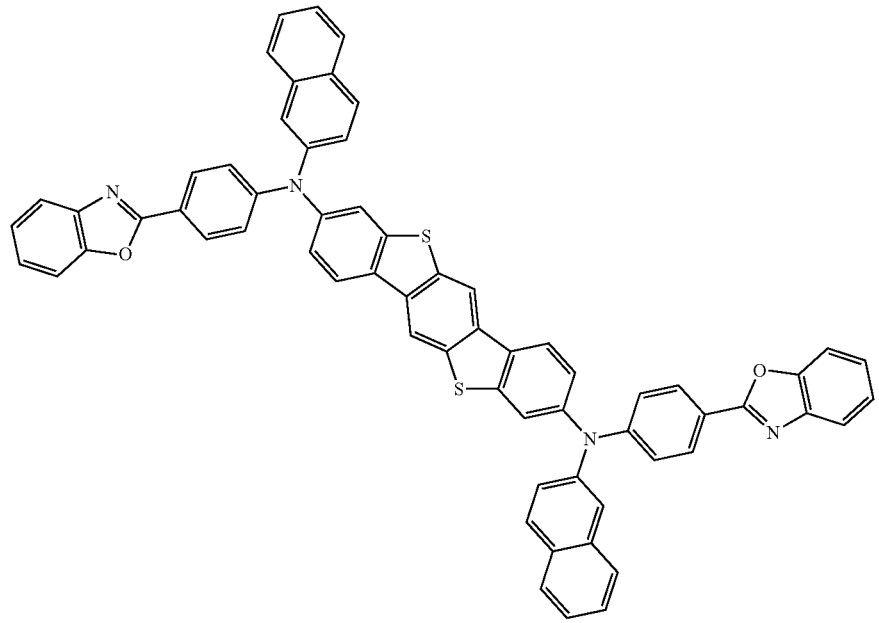
M7
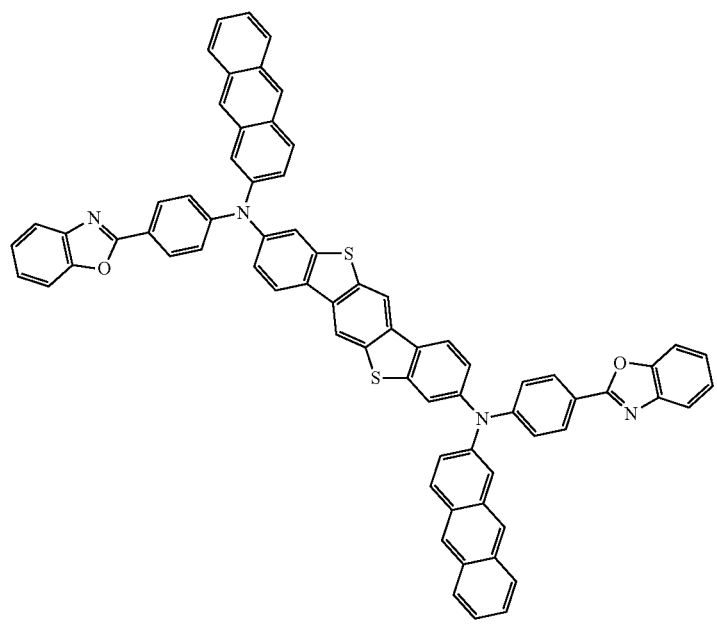
M8

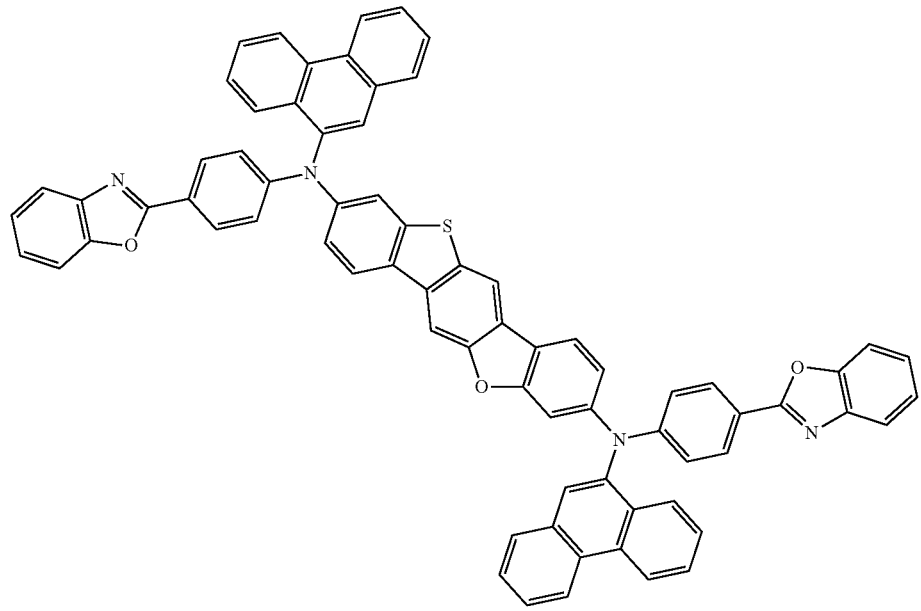
M9
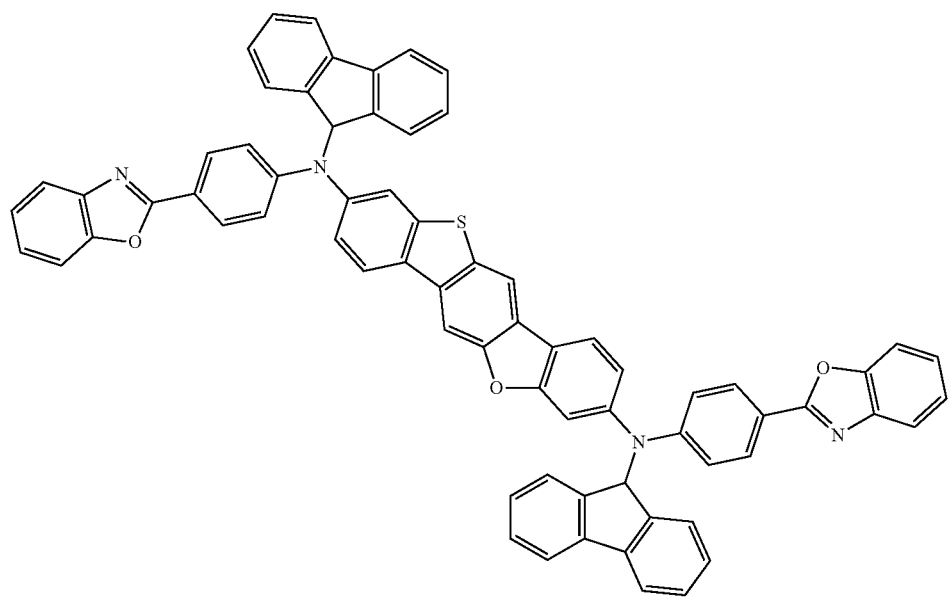
M10

-continued
M11
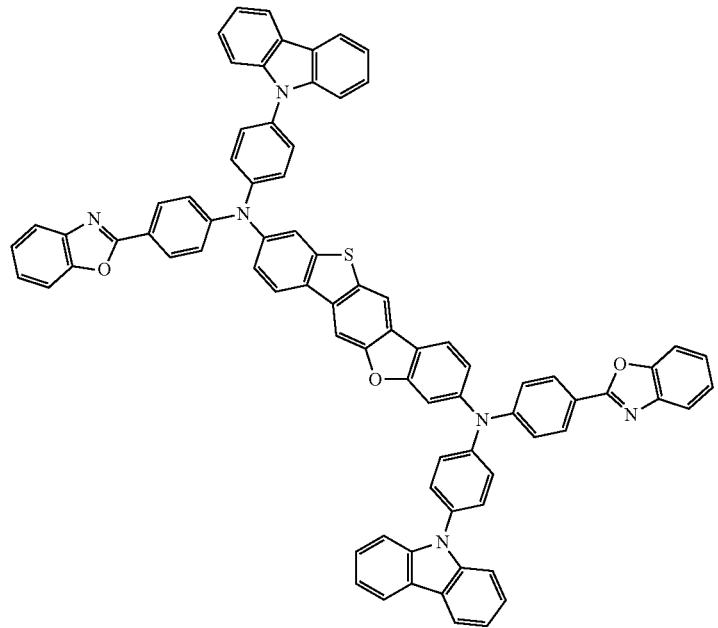
M12
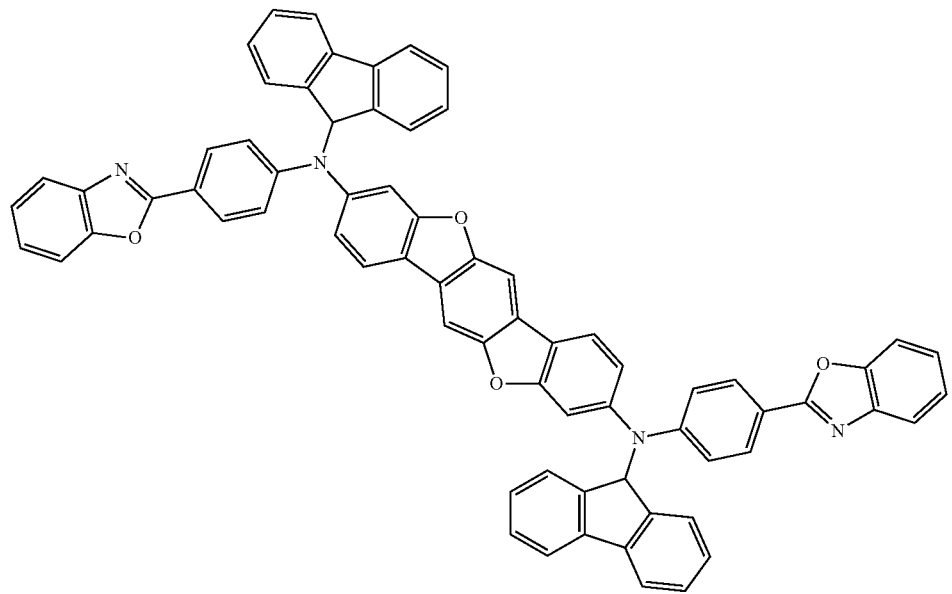
M13
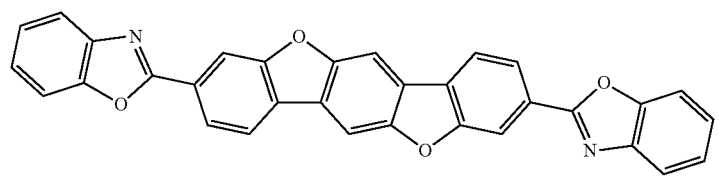

-continued
M14
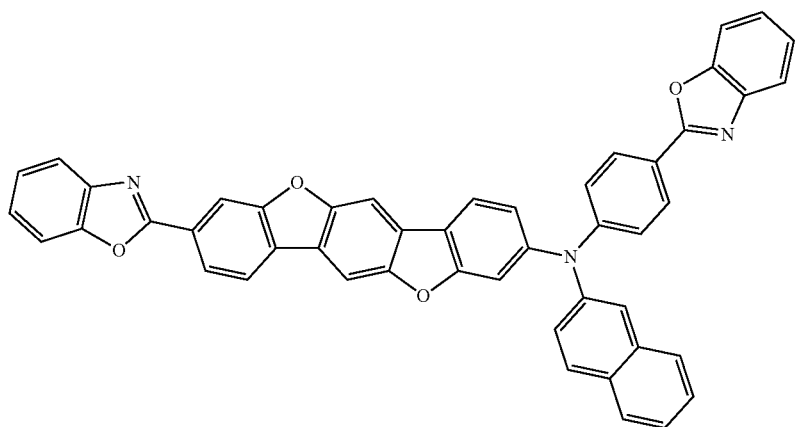
M15
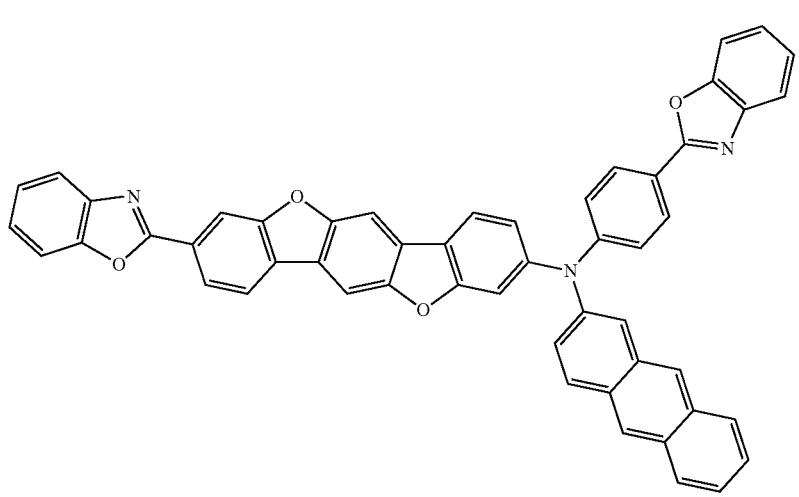
M16
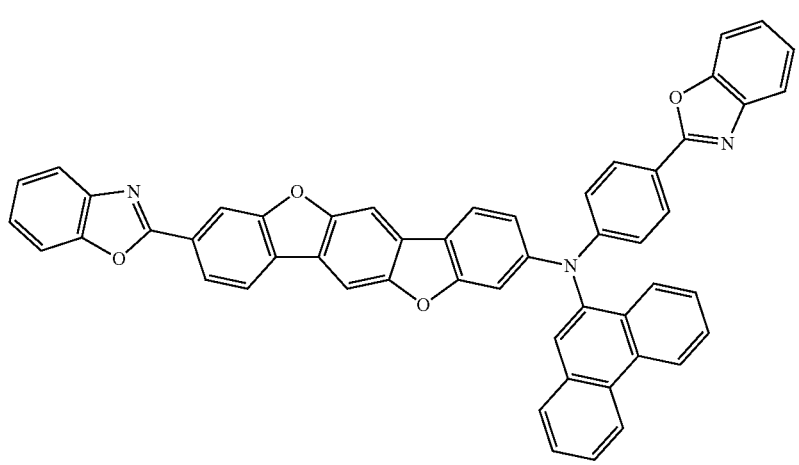

-continued
M17
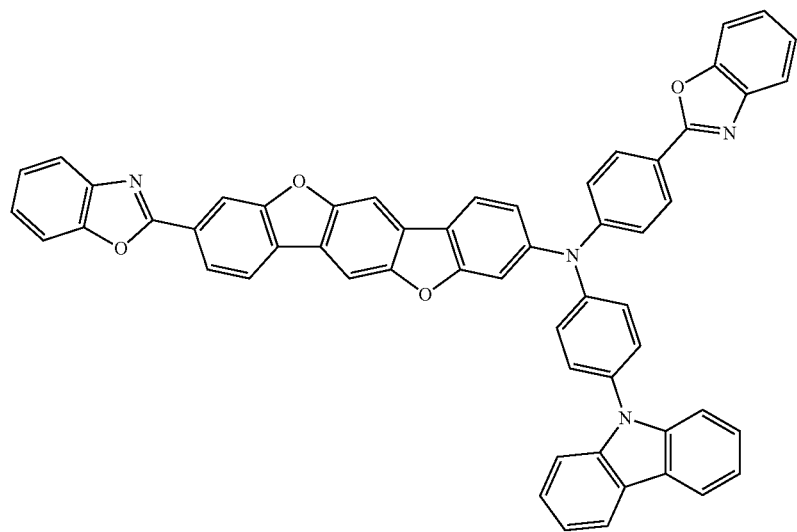
M18
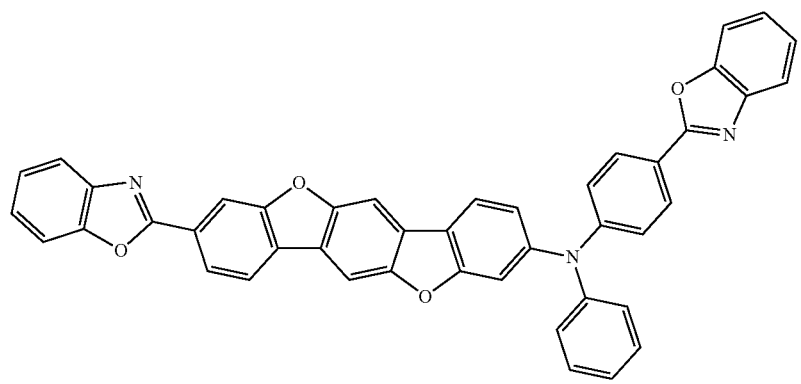
M19
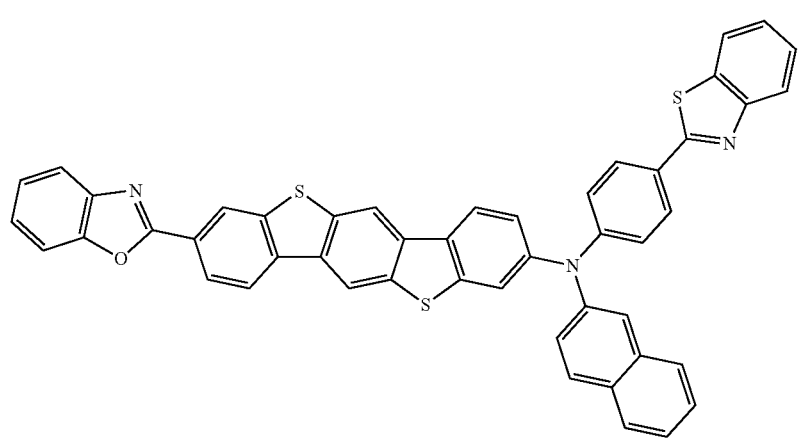

-continued
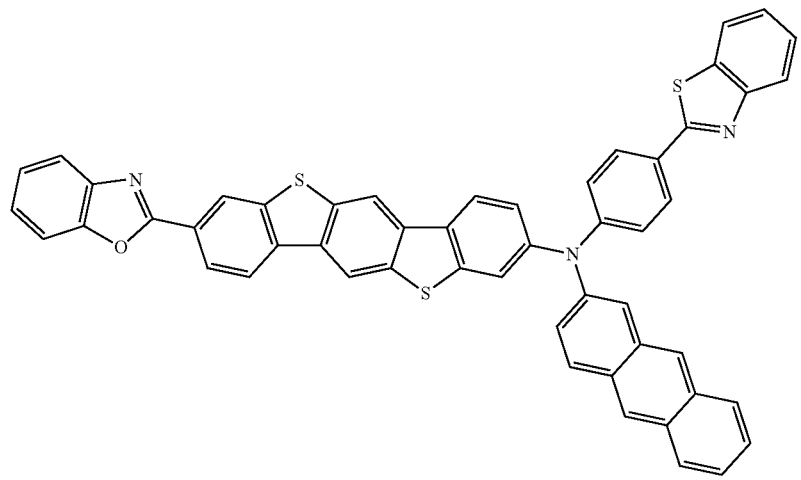
M20
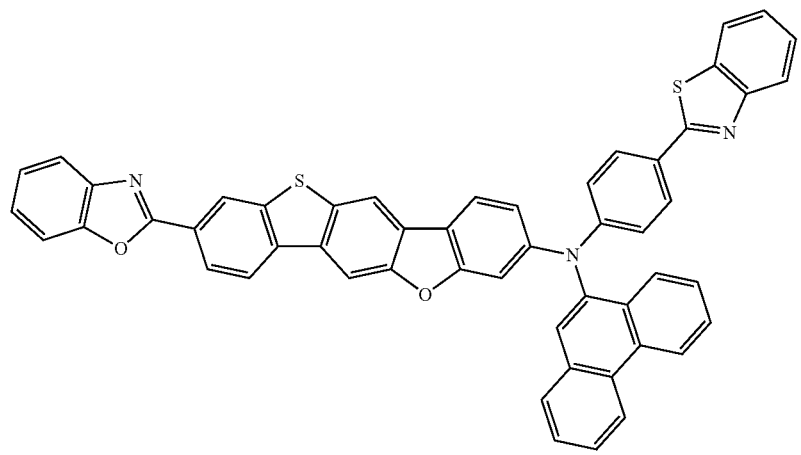
M21
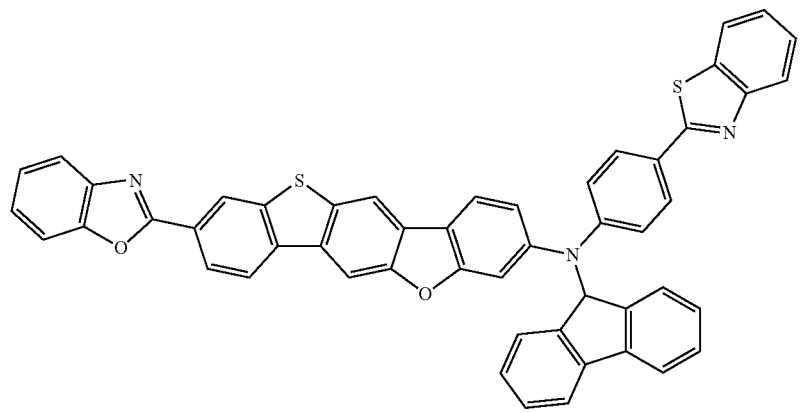
M22

M23
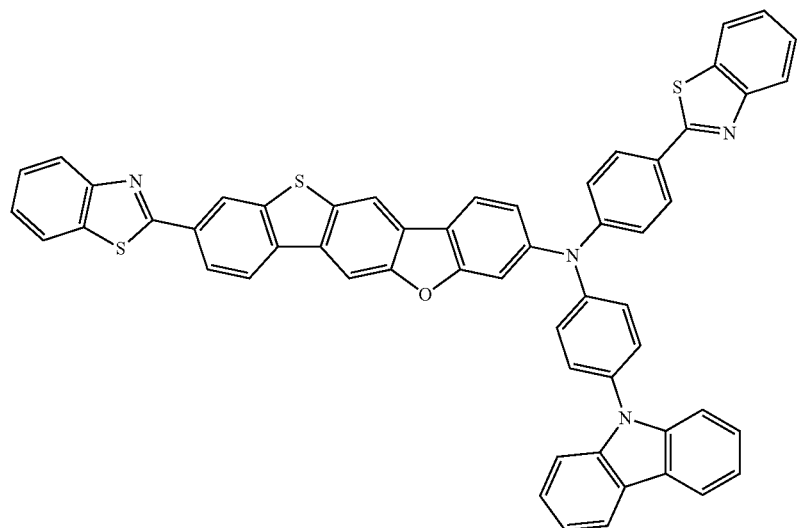
M24
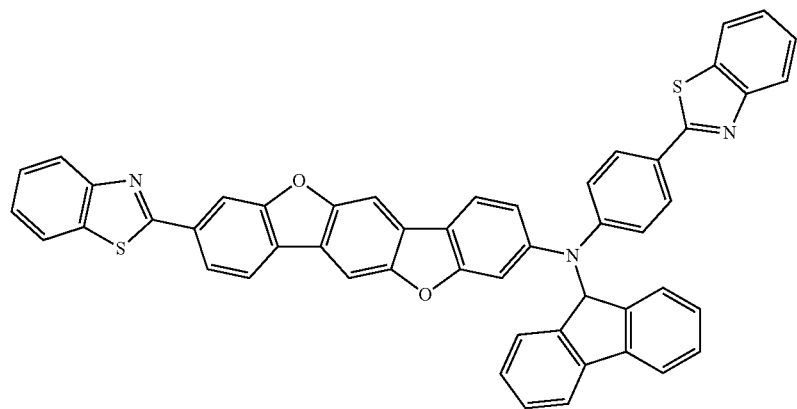
M25
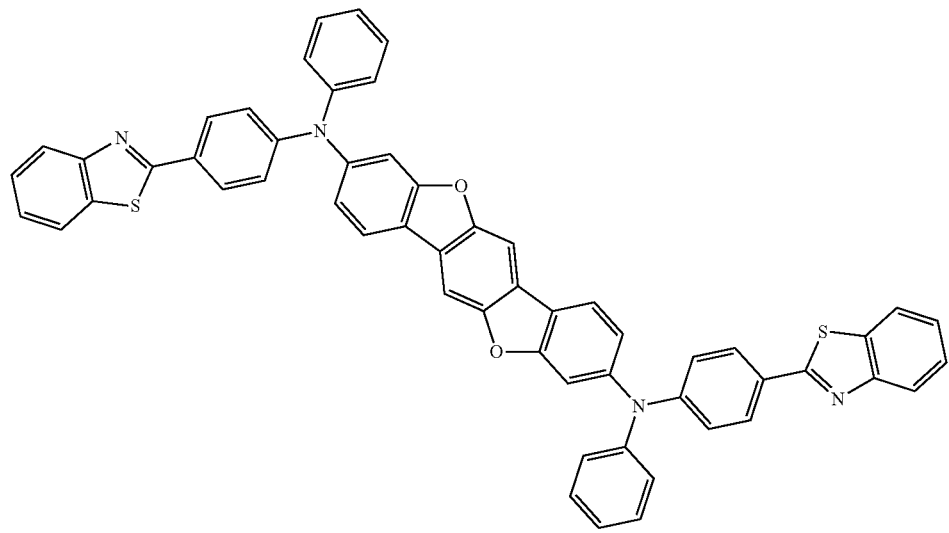

M26
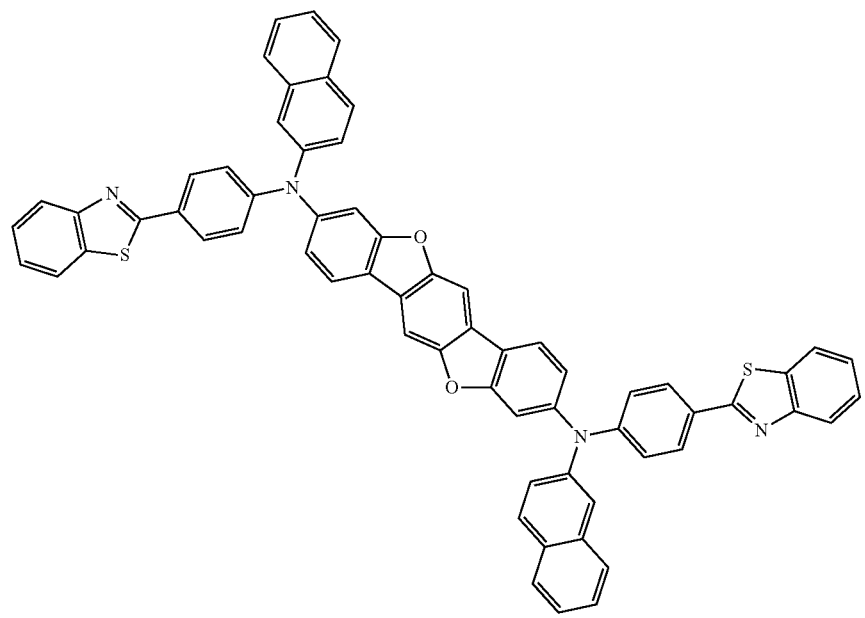
M27

-continued
M28
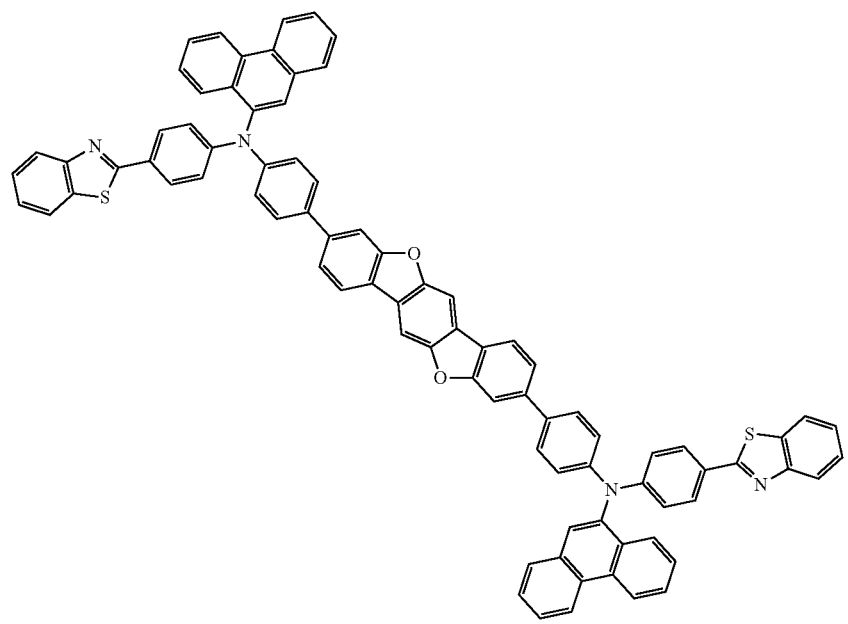
M29

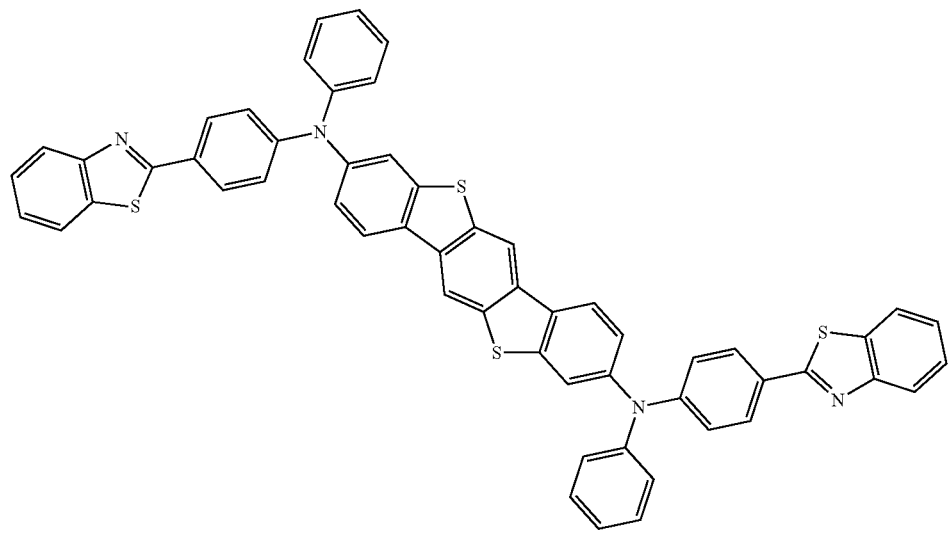
M30
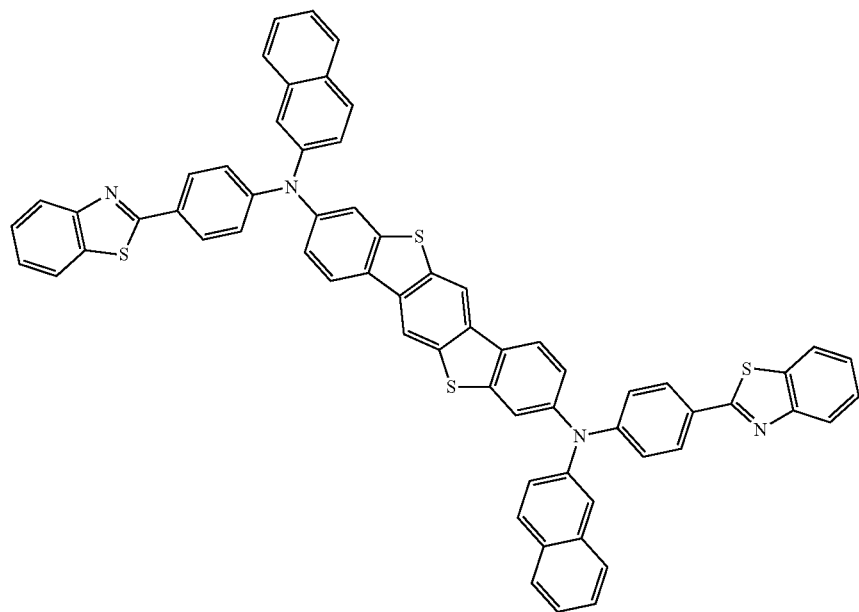
M31

-continued
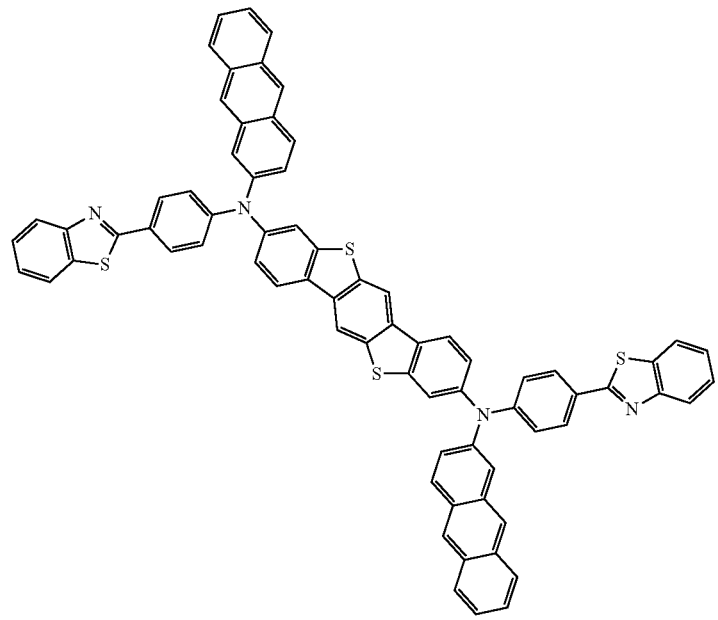
M32
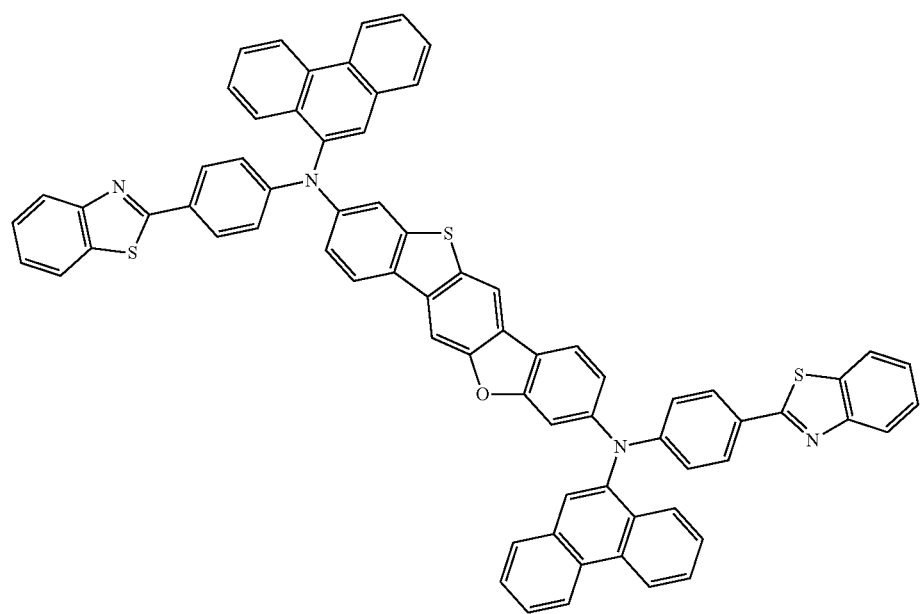
M33

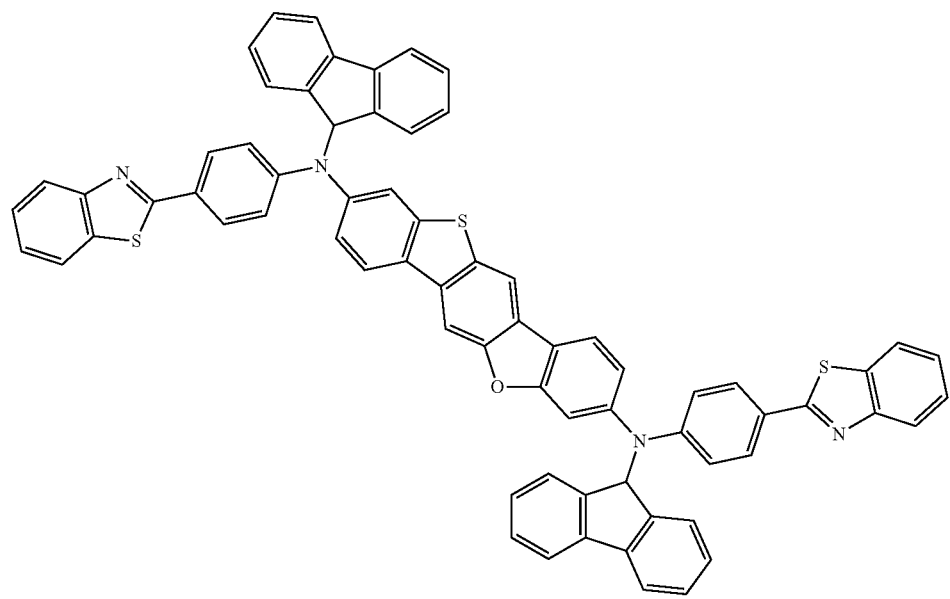

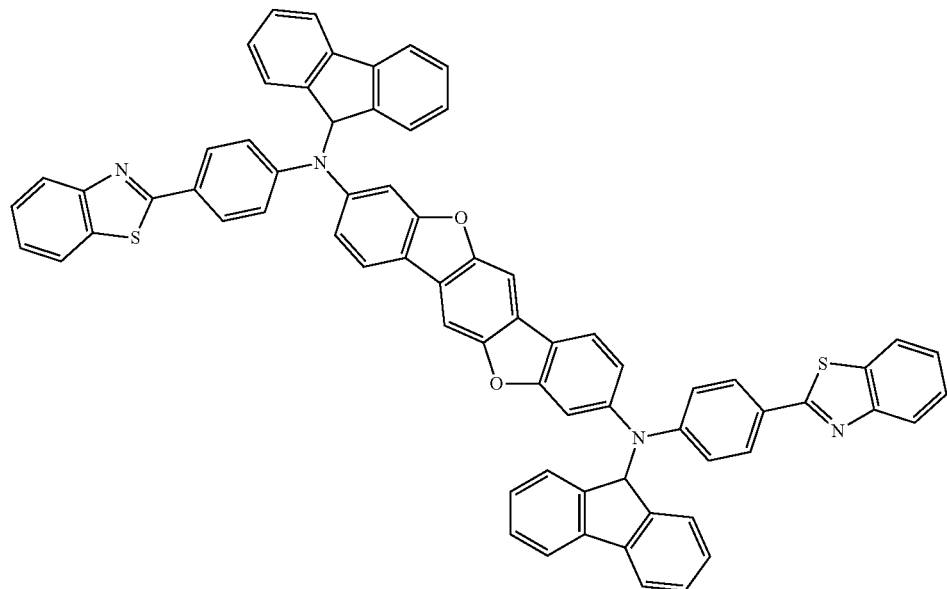
M36
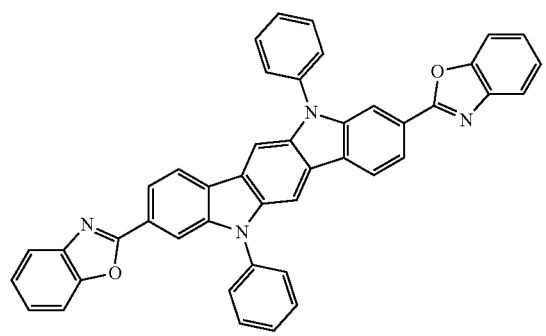
M37
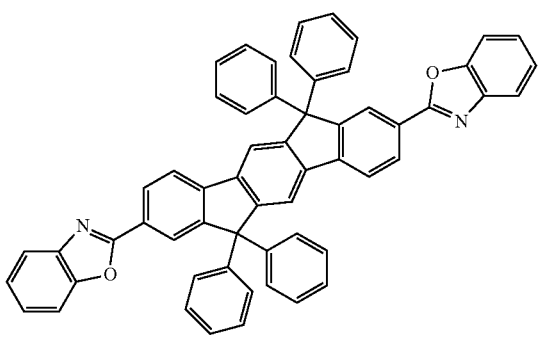
M38
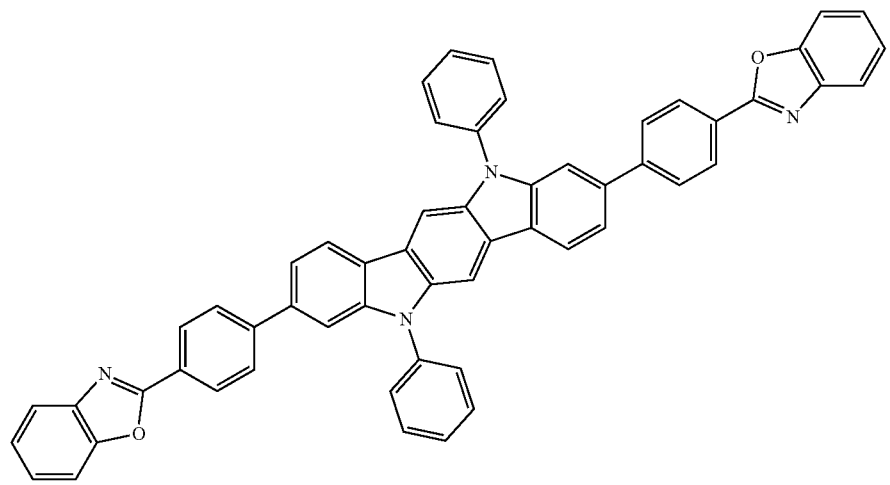
M39

M40
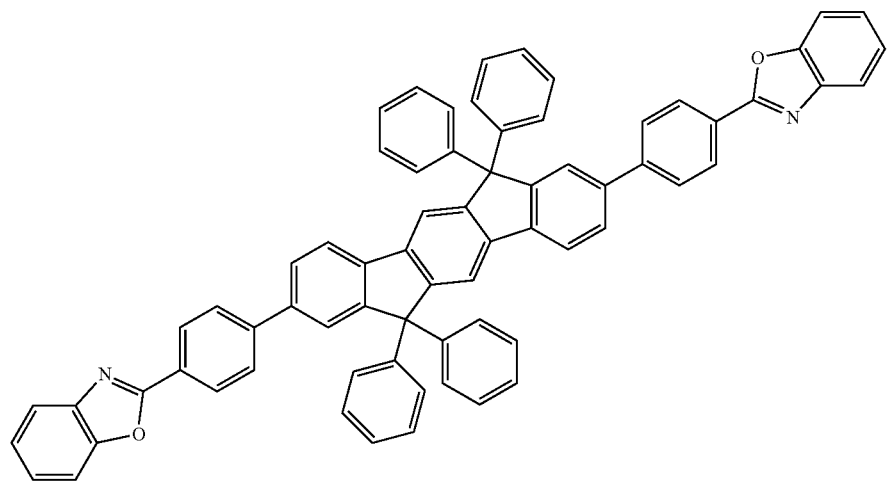
M41
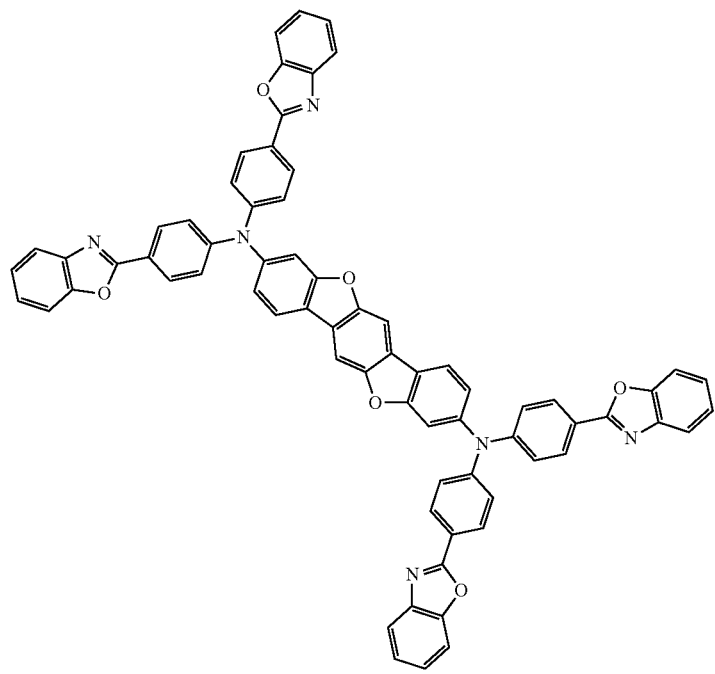
M42
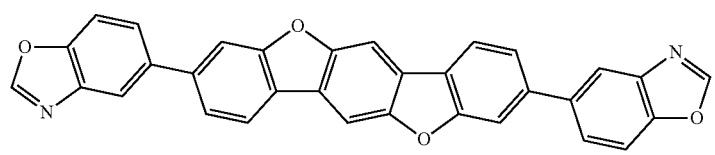
M43
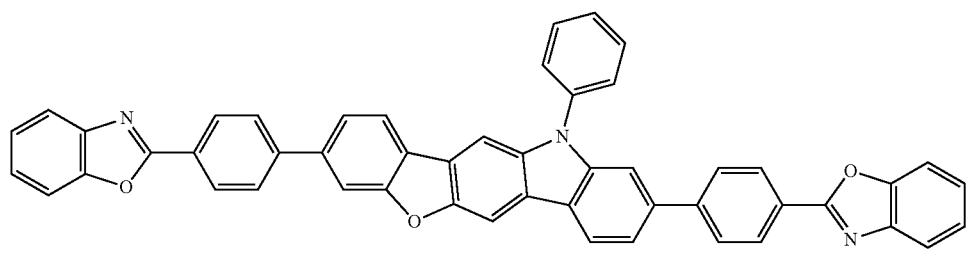

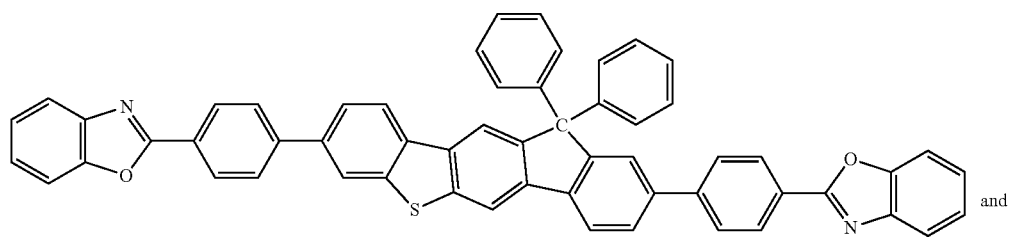

M44 and

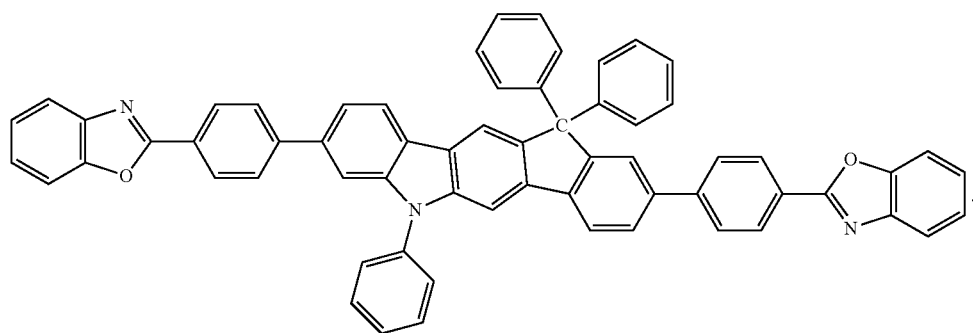

M45

A second object of the present disclosure is to provide a material for an organic electroluminescent device. The material for an organic electroluminescent device includes any one or a combination of at least two of the compound as described for the first object.

A third object of the present disclosure is to provide an organic electroluminescent device. The organic electroluminescent device includes a first electrode layer, an organic function layer and a second electrode layer which are stacked in sequence.

The organic function layer includes the material as described for the second object.

In the present disclosure, one of the first electrode layer and the second electrode layer is an anode layer and the other of the first electrode layer and the second electrode layer is a cathode layer. In one embodiment, the first electrode layer is an anode layer and the second electrode layer is a cathode layer, or the first electrode layer is a cathode layer and the second electrode layer is an anode layer.

A fourth object of the present disclosure is to provide an organic electroluminescent device. The organic electroluminescent device includes a first capping layer, a first electrode layer, an organic function layer and a second electrode layer which are stacked in sequence.

The first capping layer includes the material as described for the second object.

When the device is a top emitting device, the first electrode layer is a cathode layer and the second electrode layer is an anode layer; when the device is a bottom emitting device, the first electrode layer is an anode layer and the second electrode layer is a cathode layer.

In an embodiment, the organic electroluminescent device provided by the present disclosure, as shown in FIG. 1, includes a substrate 1, an anode 2, a hole injection layer 3, a first hole transport layer 4, a second hole transport layer 5, a light-emitting layer 6, a first electron transport layer 7, a second electron transport layer 8, a cathode 9 and a first capping layer 10.

In an embodiment, the organic electroluminescent device further includes a second capping layer disposed on a side of the first capping layer facing away from the first electrode layer, where the second capping layer includes lithium fluoride and/or a material containing small organic molecules with a refractive index of 1.40-1.65 (for example, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64 or the like).

The organic electroluminescent device provided by the present disclosure preferably includes two capping layers, and the compound provided by the present disclosure cooperates with lithium fluoride and/or a material containing small organic molecules with a refractive index of 1.40-1.65, which can alleviate the total reflection of light by a packaging glass, facilitate the transmission of visible light through the glass and improve the light extraction effect.

Figure 2:
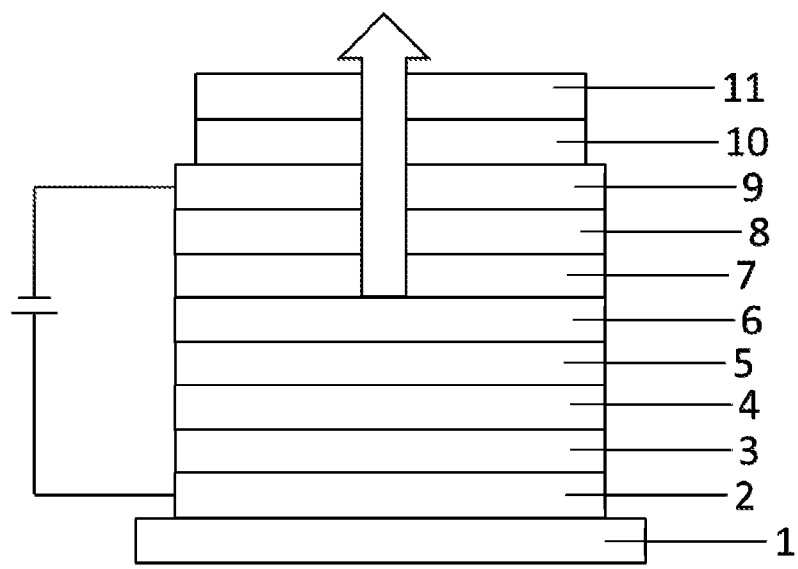
FIG. 2 is a structure diagram of an organic electroluminescent device according to another embodiment of the present disclosure.

In an embodiment, an organic electroluminescent device provided by the present disclosure, as shown in FIG. 2, includes a substrate 1, an anode 2, a hole injection layer 3, a first hole transport layer 4, a second hole transport layer 5, a light-emitting layer 6, a first electron transport layer 7, a second electron transport layer 8, a cathode 9, a first capping layer 10 and a second capping layer 11.

In an embodiment, the material containing small organic molecules with a refractive index of 1.40-1.65 includes, but is not limited to, any one or a combination of at least two of polyfluorocarbons, boron-containing compounds, silicon-containing compounds, oxygen-containing silicon compounds and adamantane-containing alkane compounds.

A fifth object of the present disclosure is to provide a display panel. The display panel includes the organic electroluminescent device as described for the fourth object.

In an embodiment, the display panel is a foldable display panel.

When the compound provided by the present disclosure is used in the foldable display panel for display at multiple angles, light extraction Δn is small for RGB colors, which can effectively reduce a color cast.

A sixth object of the present disclosure is to provide a display device. The display device includes the display panel as described for the fifth object.

The method for preparing the compound provided by the present disclosure belongs to the related art. The present disclosure provides only an exemplary synthesis route and is not limited to the following synthesis routes.

The representative synthesis route of the compound of Formula (1) provided by the present disclosure is as follows:

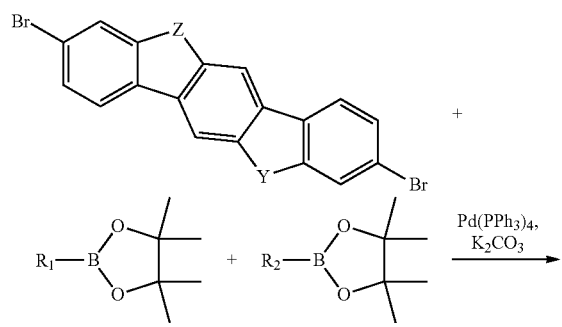

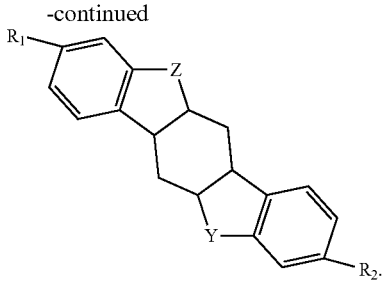

The following examples exemplarily provide specific synthesis methods for a series of compounds. For compounds whose specific synthesis methods are not mentioned, these compounds may be synthesized by similar methods or other existing methods, which are not specifically limited in the present disclosure.

Example 1

Synthesis of Compound M1

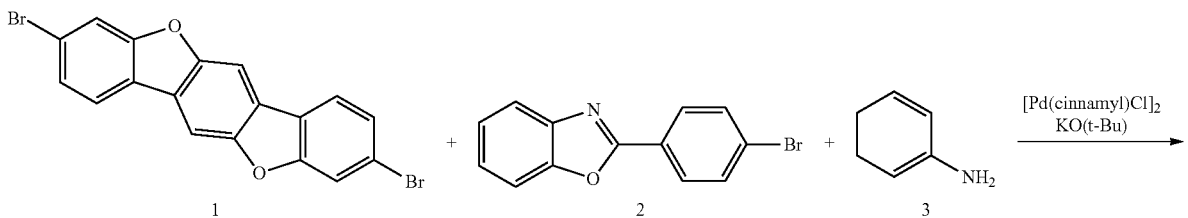

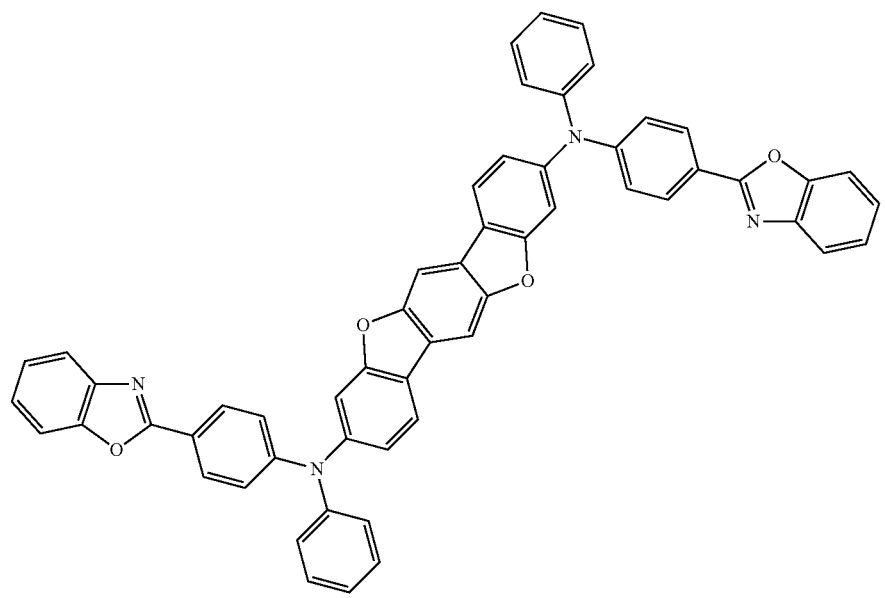

M1

A specific preparation method specifically includes steps described below.

Compound 1 (0.5 mmol), Compound 2 (0.5 mmol), Compound 3 (1.5 mmol), KO(t-Bu) (0.75 mmol) and [Pd(cinnamyl)Cl]$_2$ (0.2 mmol) were added to 3 mL of toluene and mixed into a solution, and the solution was put in a 50 mL flask and reacted at 80° C. for 12 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product M1 was obtained through column chromatography.

The structure of the target product M1 was tested through matrix-assisted laser desorption/ionization time-of-flight mass spectrometry (MALDI-TOF-MS) (m/z) to obtain $C_{56}H_{34}N_4O_4$ whose calculated value was 826.9 and measured value was 826.7.

Elemental analysis: theoretical value: C, 81.34; H, 4.14; N, 6.78; measured value: C, 81.35; H, 4.15; N, 6.78.

Example 2

Synthesis of Compound M7

A specific preparation method specifically includes steps described below.

Compound 3 (0.5 mmol), Compound 4 (0.5 mmol), Compound 5 (1.5 mmol), KO(t-Bu) (0.75 mmol) and [Pd(cinnamyl)Cl]$_2$ (0.2 mmol) were added to 3 mL of toluene and mixed into a solution, and the solution was put in a 50 mL flask and reacted at 80° C. for 12 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product M7 was obtained through column chromatography.

The structure of the target product M7 was tested through matrix-assisted laser desorption/ionization time-of-flight mass spectrometry (MALDI-TOF-MS) (m/z) to obtain $C_{64}H_{38}N_4O_2S_2$ whose calculated value was 959.1 and measured value was 959.0.

Elemental analysis: theoretical value: C, 80.14; H, 3.99; N, 5.84; measured value: C, 80.15; H, 3.98; N, 5.85.

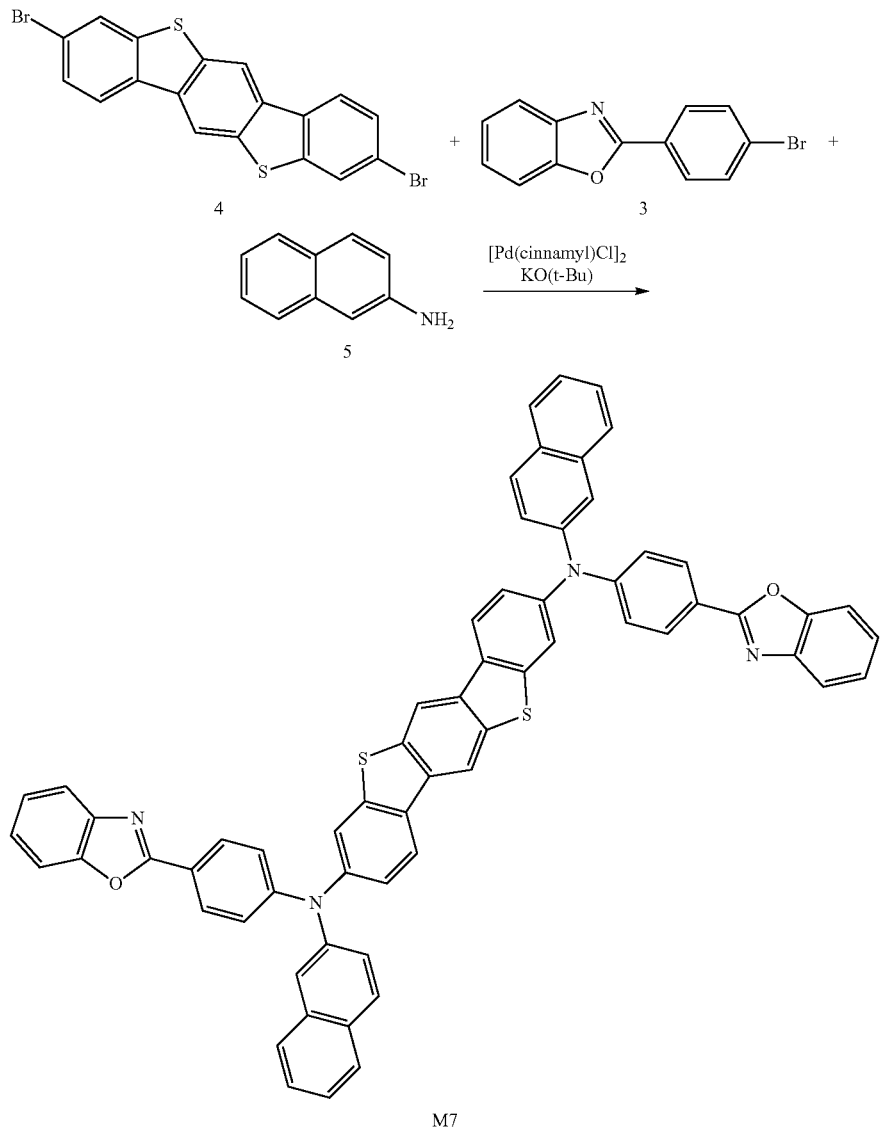

M7

Example 3

Synthesis of Compound M11

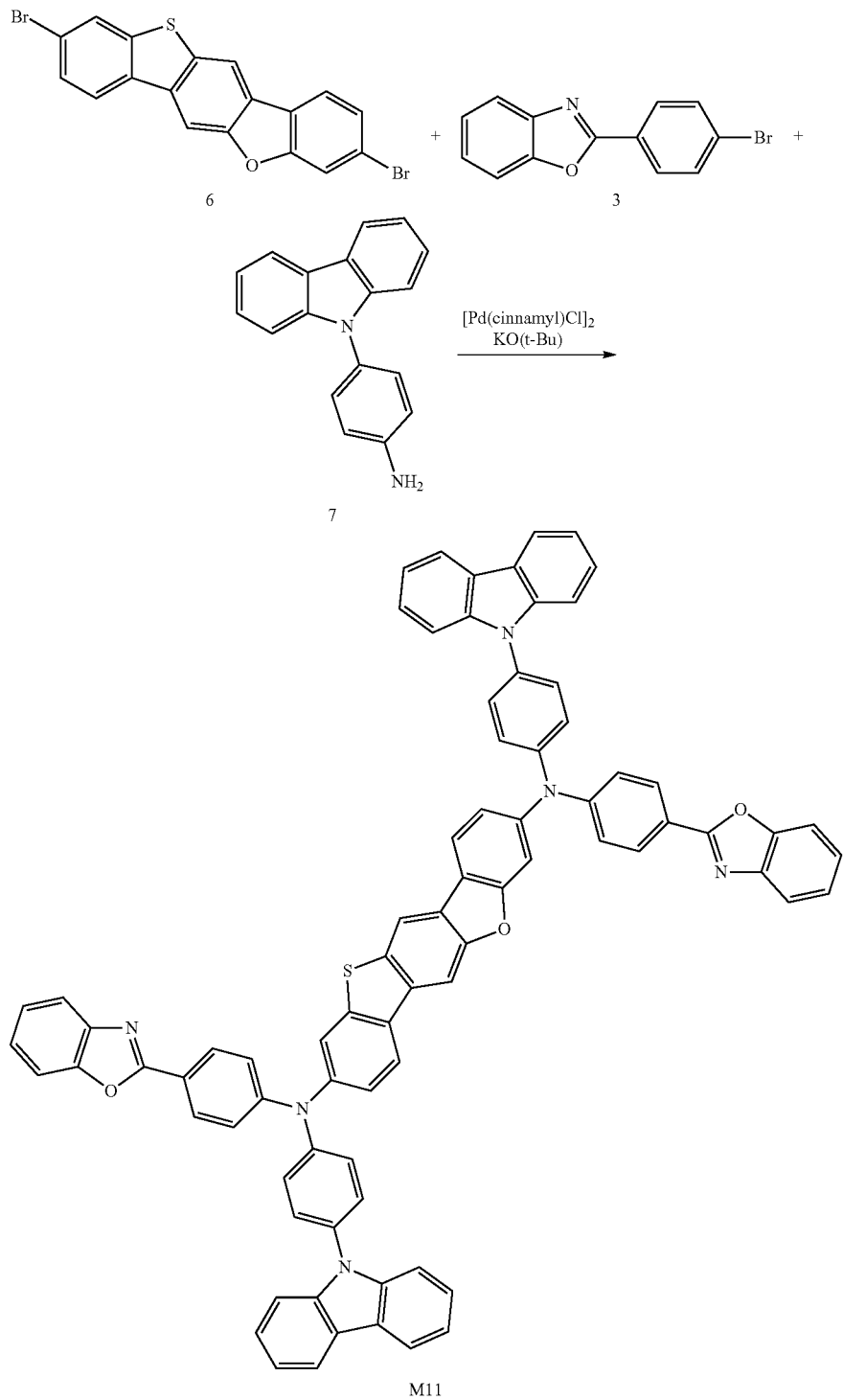

A specific preparation method specifically includes steps described below.

Compound 6 (0.5 mmol), Compound 3 (0.5 mmol), Compound 7 (1.5 mmol), KO(t-Bu) (0.75 mmol) and [Pd(cinnamyl)Cl]$_2$ (0.2 mmol) were added to 3 mL of toluene and mixed into a solution, and the solution was put in a 50 mL flask and reacted at 80° C. for 12 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product M11 was obtained through column chromatography.

The structure of the target product M11 was tested through matrix-assisted laser desorption/ionization time-of-flight mass spectrometry (MALDI-TOF-MS) (m/z) to obtain $C_{84}H_{48}N_6O_3S$ whose calculated value was 1173.3 and measured value was 1173.1.

Elemental analysis: theoretical value: C, 81.89; H, 4.12; N, 7.16; measured value: C, 81.87; H, 4.10; N, 7.15.

Example 4

Synthesis of Compound M13

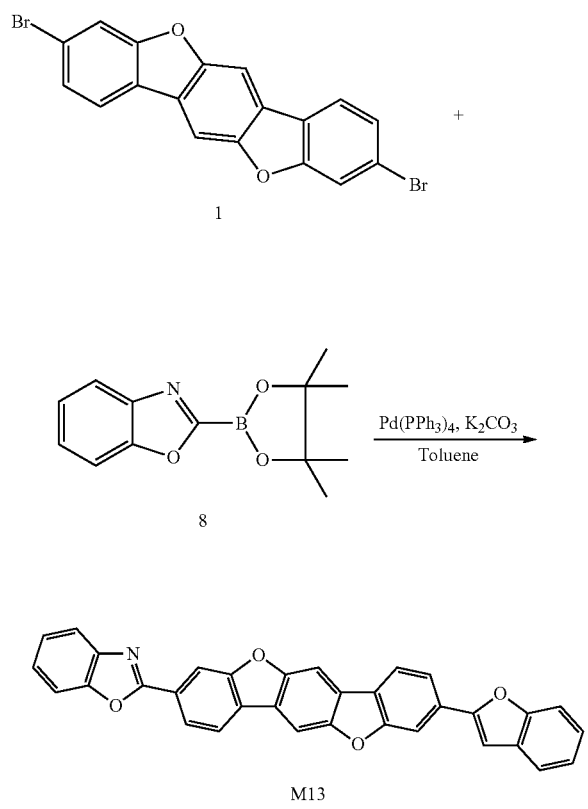

A specific preparation method specifically includes steps described below.

Compound 1 (0.5 mmol), Compound 8 (0.75 mmol), $K_2CO_3$ (0.5 mmol), $PdCl_2$ ($5\times10^{-4}$ mmol) and $Pd(pph_3)_4$ ($5\times10^{-4}$ mmol) were added to 3 mL of toluene and mixed into a solution, and the solution was put in a 50 mL flask and reacted at 100° C. for 24 h. Then the solution was cooled to room temperature and slowly added with a saturated aqueous solution of $MgSO_4$ and ethyl acetate to be extracted for three times. Then, the organic layer passed through a rotary evaporator for the solvent to be removed and the crude product M13 was obtained through column chromatography.

The structure of the target product M13 was tested through matrix-assisted laser desorption/ionization time-of-flight mass spectrometry (MALDI-TOF-MS) (m/z) to obtain $C_{32}H_{16}N_2O_4$ whose calculated value was 492.5 and measured value was 492.3.

Elemental analysis: theoretical value: C, 78.04; H, 3.27; N, 5.69; measured value: C, 78.03; H, 3.25; N, 7.13.

Example 5

Synthesis of Compound M20

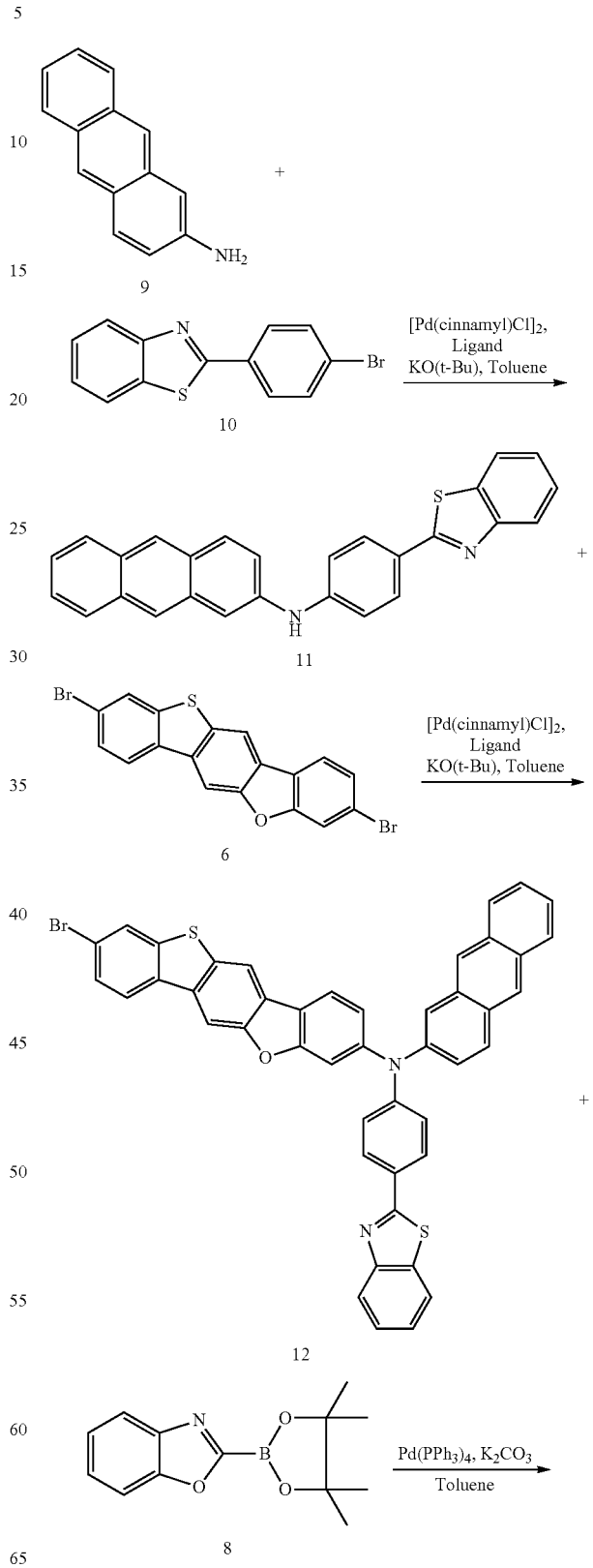

-continued

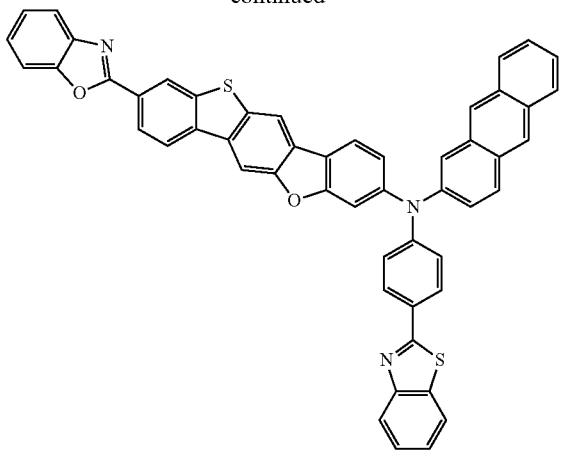

M20

A specific preparation method specifically includes steps described below.

(1) Compound 9 (0.5 mmol), Compound 10 (4.5 mmol), XPhos (0.15 mol %), KO(t-Bu) (0.75 mmol) and [Pd(cinnamyl)Cl]$_2$ (0.2 mmol) were added to 3 mL of toluene and mixed into a solution, and the solution was put in a 50 mL flask and reacted at 80° C. for 12 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product 11 was obtained through column chromatography.

(2) Compound 11 (0.5 mmol), Compound 6 (4.5 mmol), XPhos (0.15 mol %), KO(t-Bu) (0.75 mmol) and [Pd(cinnamyl)Cl]$_2$ (0.2 mmol) were added to 3 mL of toluene and mixed into a solution, and the solution was put in a 50 mL flask and reacted at 80° C. for 12 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product 12 was obtained through column chromatography.

(3) Compound 12 (0.5 mmol), Compound 8 (0.75 mmol), K$_2$CO$_3$ (0.5 mmol), PdCl$_2$ (5×10$^{-4}$ mmol) and Pd(pph$_3$)$_4$ (5×10$^{-4}$ mmol) were added to 3 mL of toluene and mixed into a solution, and the solution was put in a 50 mL flask and reacted at 100° C. for 24 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product M20 was obtained through column chromatography.

The structure of the target product M20 was tested through matrix-assisted laser desorption/ionization time-of-flight mass spectrometry (MALDI-TOF-MS) (m/z) to obtain C$_{52}$H$_{29}$N$_3$O$_2$S$_2$ whose calculated value was 807.15 and measured value was 807.13.

Elemental analysis: theoretical value: C, 77.30; H, 3.62; N, 5.20; measured value: C, 77.29; H, 3.64; N, 5.19.

Example 6

Synthesis of Compound M41

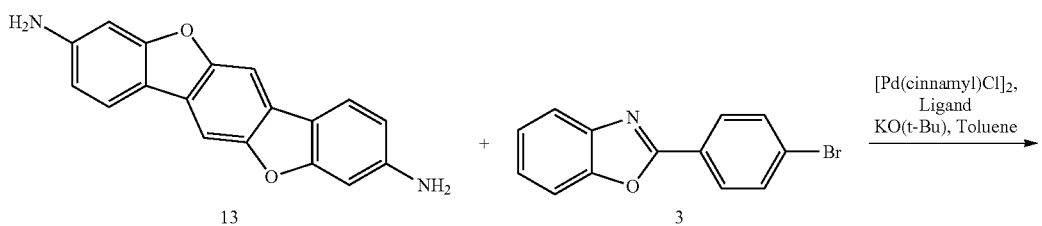

-continued

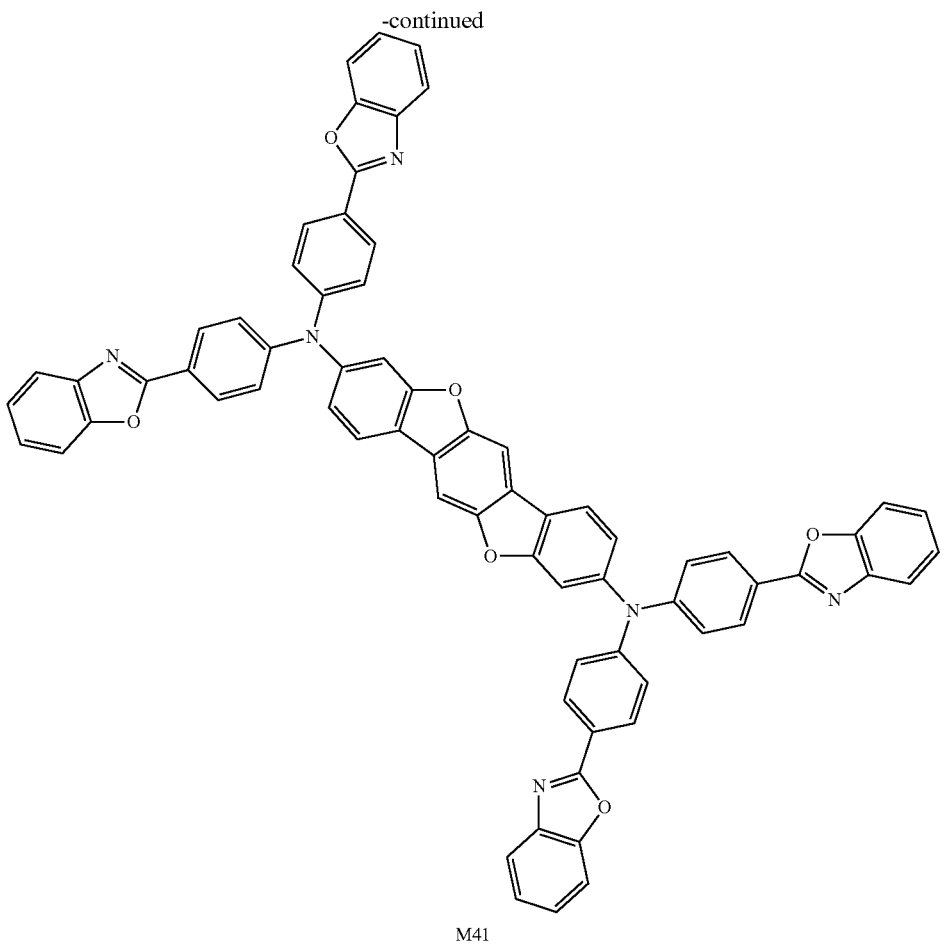

M41

A specific preparation method specifically includes steps described below.

Compound 13 (0.5 mmol), Compound 3 (4.5 mmol), XPhos (0.15 mol %), KO(t-Bu) (0.75 mmol) and [Pd(cinnamyl)Cl]$_2$ (0.2 mmol) were added to 3 mL of toluene and mixed into a solution, and the solution was put in a 50 mL flask and reacted at 80° C. for 12 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product M41 was obtained through column chromatography.

The structure of the target product M41 was tested through matrix-assisted laser desorption/ionization time-of-flight mass spectrometry (MALDI-TOF-MS) (m/z) to obtain $C_{70}H_{40}N_6O_6$ whose calculated value was 1060.10 and measured value was 1060.00.

Elemental analysis: theoretical value: C, 79.23; H, 3.80; N, 7.92; measured value: C, 79.22; H, 3.80; N, 7.91.

Example 7

Synthesis of Compound M42

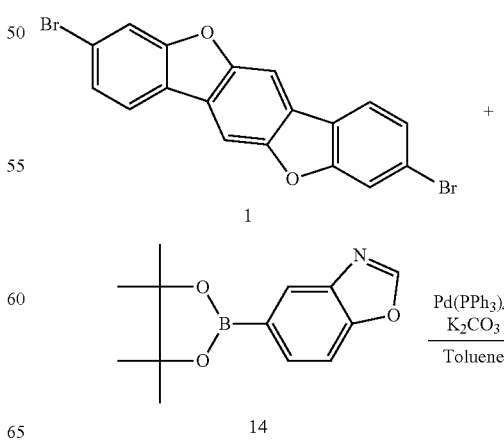

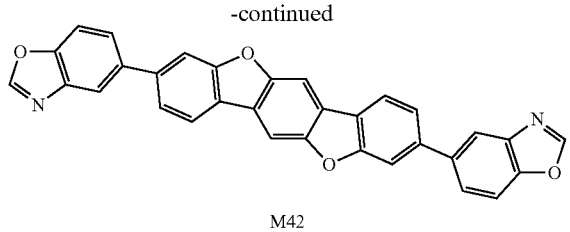

M42

A specific preparation method specifically includes steps described below.

Compound 1 (0.5 mmol), Compound 14 (0.75 mmol), K$_2$CO$_3$ (0.5 mmol), PdCl$_2$ (5×10$^{-4}$ mmol) and Pd(pph$_3$)$_4$ (5×10$^{-4}$ mmol) were added to 3 mL of toluene and mixed into a solution, and the solution was put in a 50 mL flask and reacted at 100° C. for 24 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product M42 was obtained through column chromatography.

The structure of the target product M42 was tested through matrix-assisted laser desorption/ionization time-of-flight mass spectrometry (MALDI-TOF-MS) (m/z) to obtain C$_{32}$H$_{16}$N$_2$O$_4$ whose calculated value was 492.48 and measured value was 492.46.

Elemental analysis: theoretical value: C, 78.04; H, 3.27; N, 5.69; measured value: C, 78.03; H, 3.25; N, 5.58.

Example 8

Synthesis of Compound M43

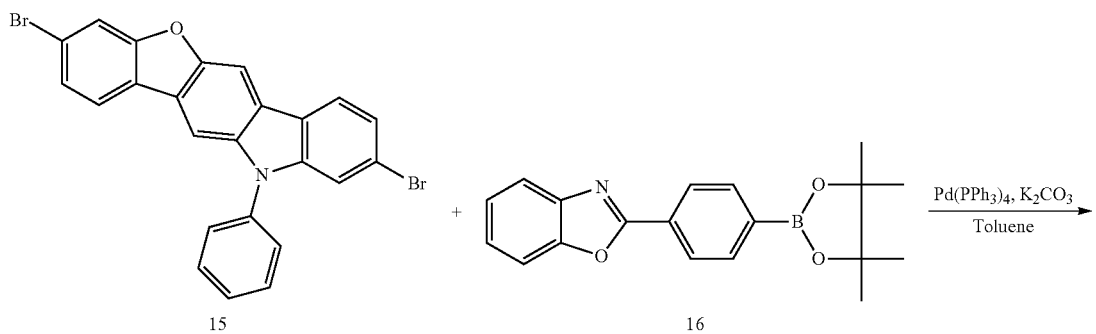

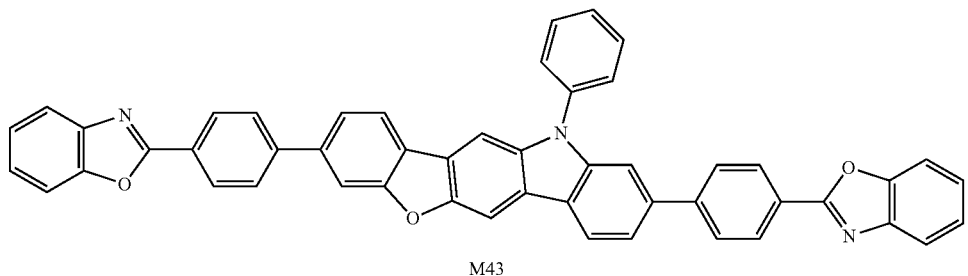

M43

A specific preparation method specifically includes steps described below.

Compound 15 (0.5 mmol), Compound 16 (0.75 mmol), K$_2$CO$_3$ (0.5 mmol), PdCl$_2$ (5×10$^{-4}$ mmol) and Pd(pph$_3$)$_4$ (5×10$^{-4}$ mmol) were added to 3 mL of toluene and mixed into a solution, and the solution was put in a 50 mL flask and reacted at 100° C. for 24 h. Then the solution was cooled to room temperature and slowly added with a saturated aqueous solution of MgSO$_4$ and ethyl acetate to be extracted for three times. Then, the organic layer passed through a rotary evaporator for the solvent to be removed and the crude product M43 was obtained through column chromatography.

The structure of the target product M43 was tested through matrix-assisted laser desorption/ionization time-of-flight mass spectrometry (MALDI-TOF-MS) (m/z) to obtain C$_{50}$H$_{29}$N$_3$O$_3$ whose calculated value was 719.78 and measured value was 719.77.

Elemental analysis: theoretical value: C, 83.43; H, 4.06; N, 5.84; measured value: C, 83.42; H, 4.05; N, 5.83.

Example 9

Synthesis of Compound M44

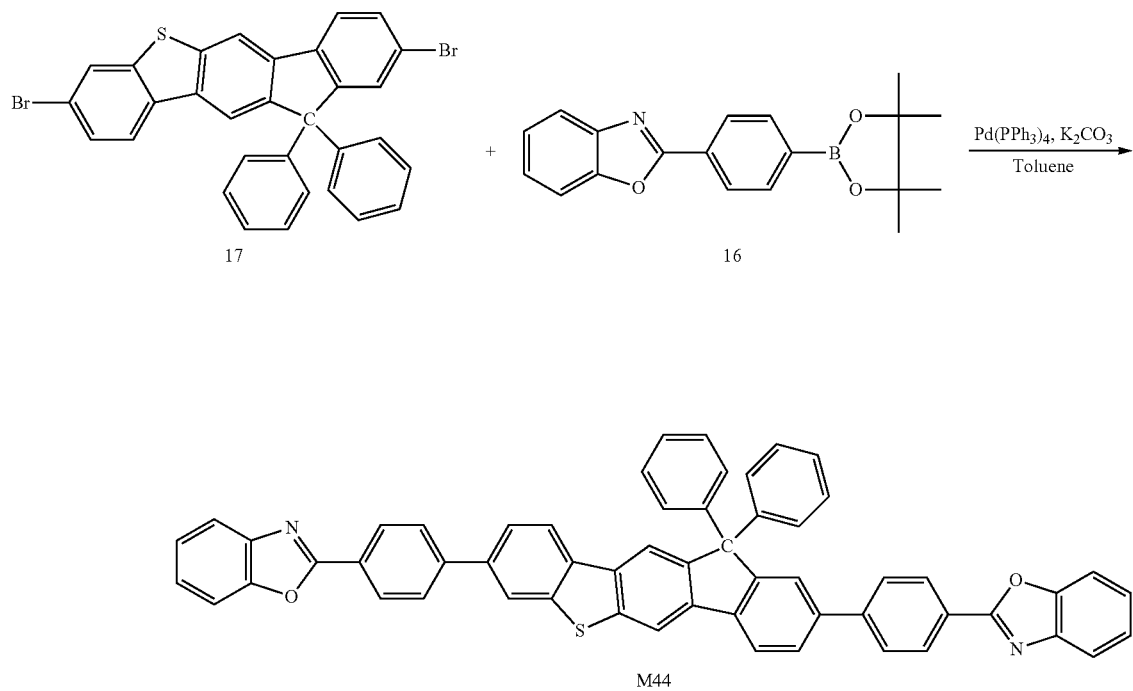

A specific preparation method specifically includes steps described below.

Compound 17 (0.5 mmol), Compound 16 (0.75 mmol), $K_2CO_3$ (0.5 mmol), $PdCl_2$ ($5\times10^{-4}$ mmol) and $Pd(pph_3)_4$ ($5\times10^{-4}$ mmol) were added to 3 mL of toluene and mixed into a solution, and the solution was put in a 50 mL flask and reacted at 100° C. for 24 h. Then the solution was cooled to room temperature and slowly added with a saturated aqueous solution of $MgSO_4$ and ethyl acetate to be extracted for three times. Then, the organic layer passed through a rotary evaporator for the solvent to be removed and the crude product M44 was obtained through column chromatography.

The structure of the target product M44 was tested through matrix-assisted laser desorption/ionization time-of-flight mass spectrometry (MALDI-TOF-MS) (m/z) to obtain $C_{57}H_{34}N_2O_2S$ whose calculated value was 810.96 and measured value was 810.95.

Elemental analysis: theoretical value: C, 84.42; H, 4.23; N, 3.45; measured value: C, 84.41; H, 4.21; N, 3.44.

Example 10

Synthesis of Compound M45

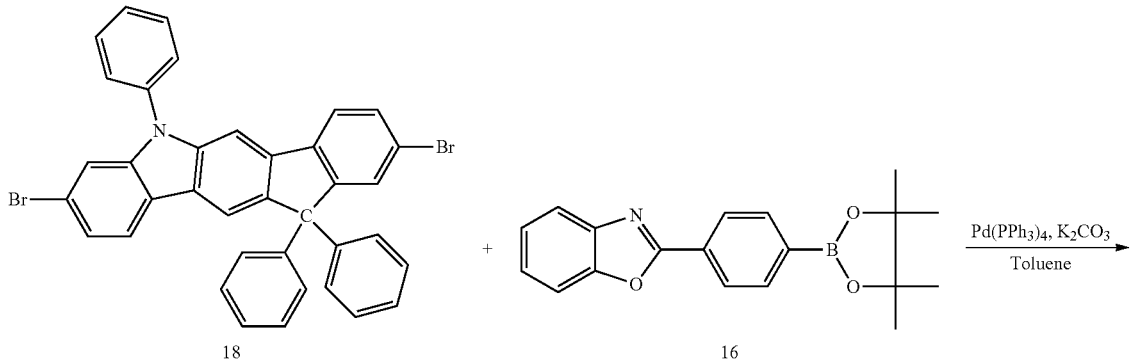

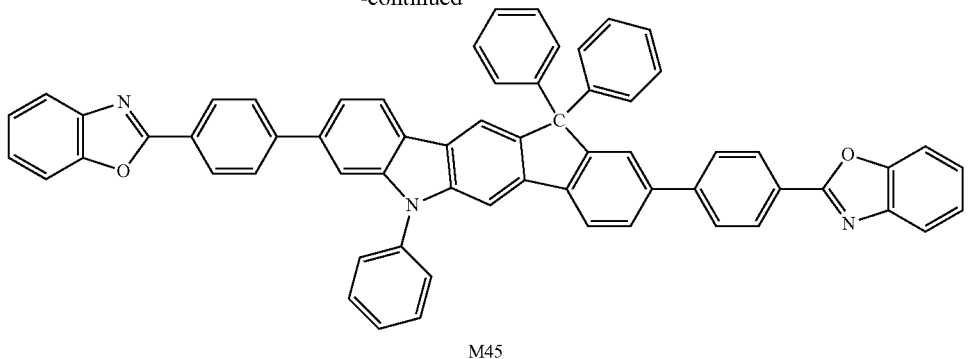

M45

A specific preparation method specifically includes steps described below.

Compound 18 (0.5 mmol), Compound 16 (0.75 mmol), $K_2CO_3$ (0.5 mmol), $PdCl_2$ ($5\times10^{-4}$ mmol) and $Pd(pph_3)_4$ ($5\times10^{-4}$ mmol) were added to 3 mL of toluene and mixed into a solution, and the solution was put in a 50 mL flask and reacted at 100° C. for 24 h. Then the solution was cooled to room temperature and slowly added with a saturated aqueous solution of $MgSO_4$ and ethyl acetate to be extracted for three times. Then, the organic layer passed through a rotary evaporator for the solvent to be removed and the crude product M45 was obtained through column chromatography.

The structure of the target product M45 was tested through matrix-assisted laser desorption/ionization time-of-flight mass spectrometry (MALDI-TOF-MS) (m/z) to obtain $C_{63}H_{39}N_3O_2$ whose calculated value was 810.96 and measured value was 810.95.

Elemental analysis: theoretical value: C, 86.97; H, 4.52; N, 4.83; measured value: C, 86.96; H, 4.51; N, 4.82.

Performance Test I Characterization of Refractive Indexes of Materials

The refractive indexes of the compounds at wavelengths of 460 nm, 530 nm and 620 nm were tested by an ellipsometer. A difference $\Delta n_1$ between the refractive index at the wavelength of 460 nm and the refractive index at the wavelength of 530 nm, a difference $\Delta n_2$ between the refractive index at the wavelength of 530 nm and the refractive index at the wavelength of 620 nm, and a difference $\Delta n_3$ between the refractive index at the wavelength of 460 nm and the refractive index at the wavelength of 620 nm were calculated.

The results of the preceding test are shown in Table 1.

TABLE 1

| Compound | $n_{460\,nm}$ | $n_{530\,nm}$ | $n_{620\,nm}$ | $\Delta n_1$ | $\Delta n_2$ | $\Delta n_3$ |
|---|---|---|---|---|---|---|
| M1  | 2.01 | 1.87 | 1.80 | 0.14 | 0.07 | 0.21 |
| M7  | 2.10 | 1.97 | 1.91 | 0.13 | 0.06 | 0.19 |
| M11 | 2.18 | 2.07 | 2.00 | 0.11 | 0.07 | 0.18 |
| M13 | 2.31 | 2.16 | 2.08 | 0.15 | 0.08 | 0.23 |
| M20 | 2.40 | 2.26 | 2.12 | 0.14 | 0.05 | 0.19 |
| M41 | 2.30 | 2.17 | 2.10 | 0.13 | 0.07 | 0.20 |
| M42 | 2.21 | 2.06 | 1.97 | 0.15 | 0.09 | 0.24 |
| M43 | 2.15 | 2.02 | 1.94 | 0.13 | 0.08 | 0.21 |
| M44 | 2.18 | 2.06 | 1.99 | 0.12 | 0.07 | 0.19 |
| M45 | 2.18 | 2.03 | 1.93 | 0.15 | 0.10 | 0.25 |
| C1  | 2.18 | 2.00 | 1.93 | 0.18 | 0.07 | 0.25 |
| C2  | 2.20 | 2.05 | 1.94 | 0.15 | 0.11 | 0.26 |

Comparative compounds C1 and C2 have the following structures:

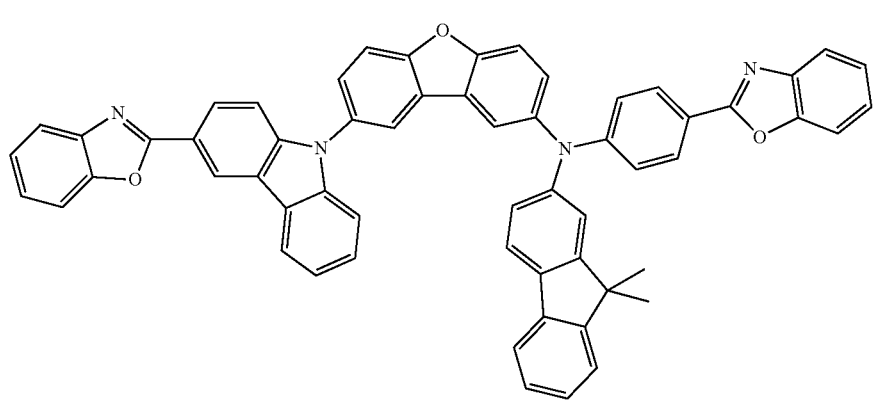

(C1)

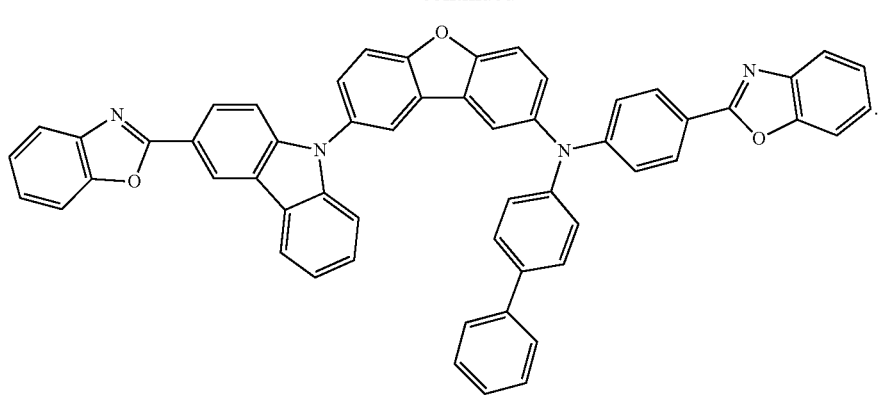

(C2)

It can be seen from Table 1 that the compounds provided by the present disclosure have relatively high refractive indexes and satisfy that the difference between the refractive index at the wavelength of 460 nm and the refractive index at the wavelength of 530 nm is 0.10-0.17, the difference between the refractive index at the wavelength of 530 nm and the refractive index at the wavelength of 620 nm is 0.03-0.10, and the difference between the refractive index at the wavelength of 460 nm and the refractive index at the wavelength of 620 nm is 0.15-0.40. These compounds can effectively improve a color cast while achieving display at multiple angles. Compounds C1 and C2 cannot satisfy the preceding conditions for the refractive index and thus cannot achieve display at multiple angles.

For a better understanding of the present disclosure, application examples of the compounds of the present disclosure are listed below. The present disclosure and not to be construed as specific limitations to the present disclosure.

Application Example 1

This application example provides an organic electroluminescent device which has a structure shown in FIG. 1 and is prepared through specific steps described below.

(1) A glass substrate with an indium tin oxide (ITO) anode layer 2 (with a thickness of 15 nm) was cut into a size of 50 mm×50 mm×0.7 mm, sonicated in isopropyl alcohol and deionized water for 30 min separately, and cleaned under ozone for 10 min. The cleaned substrate 1 was installed onto a vacuum deposition device.

(2) A material for a hole injection layer, Compound 2, and a p-doping material, Compound 1, were co-deposited at a doping ratio of 3% (mass ratio) by means of vacuum evaporation on the ITO anode layer 2 as a hole injection layer 3 with a thickness of 5 nm.

(3) A material for a hole transport layer, Compound 2, was deposited by means of vacuum evaporation on the hole injection layer 3 as a first hole transport layer 4 with a thickness of 100 nm.

(4) A hole transport material, Compound 3, was deposited by means of vacuum evaporation on the first hole transport layer 4 as a second hole transport layer 5 with a thickness of 5 nm.

(5) A light-emitting layer 6 with a thickness of 30 nm was deposited by means of vacuum evaporation on the second hole transport layer 5, where Compound 4 was doped as a host material with Compound 5 as a doping material at a ratio of 3% (mass ratio).

(6) An electron transport material, Compound 6, was deposited by means of vacuum evaporation on the light-emitting layer 6 as a first electron transport layer 7 with a thickness of 30 nm.

(7) An electron transport material, Compound 7, and a n-doping material, Compound 8, were co-deposited at a doping mass ratio of 1:1 by means of vacuum evaporation on the first electron transport layer 7 as a second electron transport layer 8 with a thickness of 5 nm.

(8) A magnesium-silver electrode was deposited at a ratio of 9:1 by means of vacuum evaporation on the second electron transport layer 8 as a cathode 9 with a thickness of 10 nm.

(9) Compound M1 of the present disclosure was deposited by means of vacuum evaporation on the cathode 9 as a capping layer 10 with a thickness of 100 nm.

The compounds used in the preceding steps have the following structures:

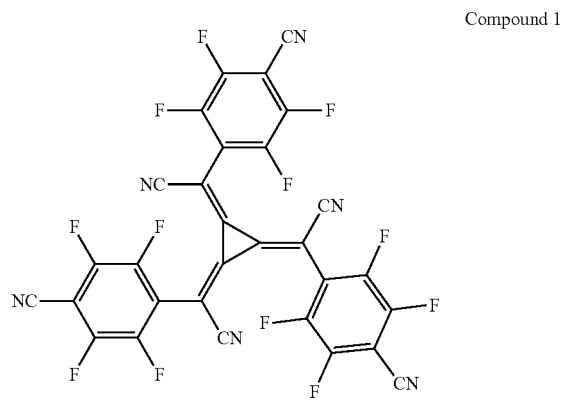

Compound 1

Compound 2
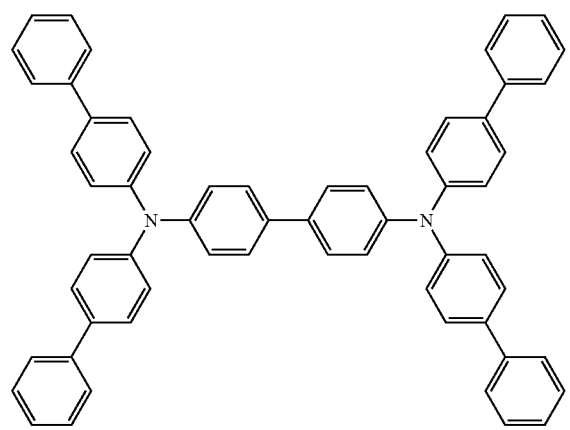

Compound 3
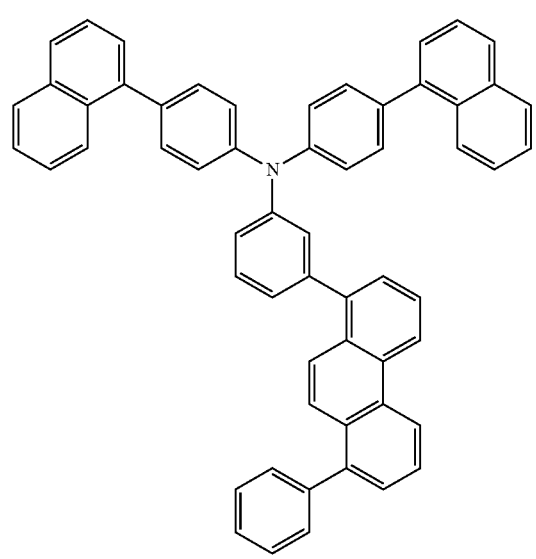

Compound 4
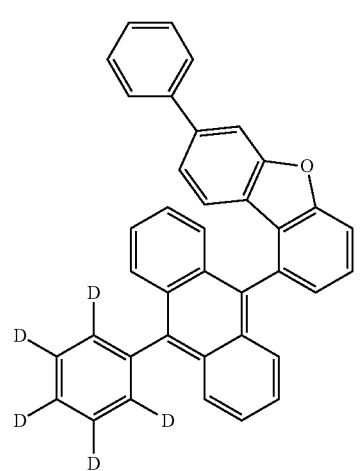

Compound 5
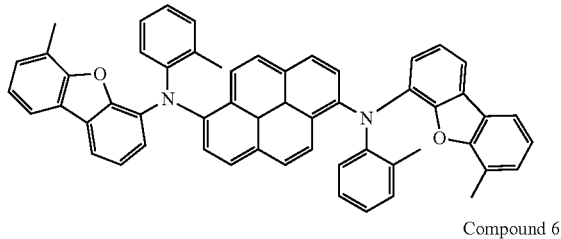

Compound 6
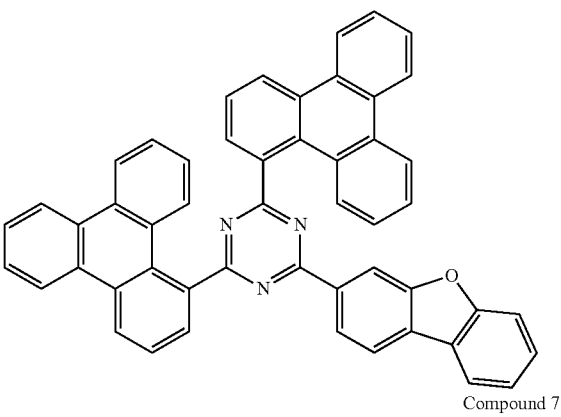

Compound 7
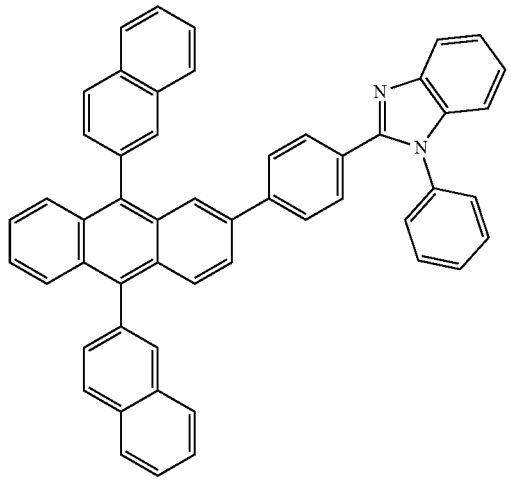

Compound 8
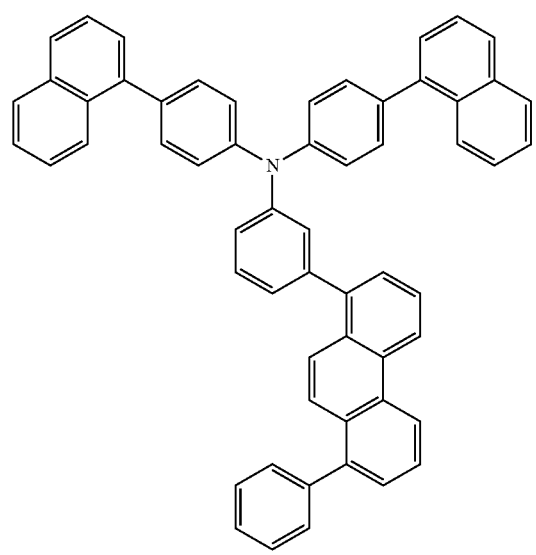

Application Examples 2-10 and Comparative Application Examples 1-2 differ from Application Example 1 only in that Compound M1 in step (9) was replaced with Compounds M7, M11, M13, M20, M41, M42, M43, M44, M45, C1 and C2 respectively for preparing the capping layer. All the other preparation steps are the same. For details, see Table 2.

Performance Test II Characterization of Device Performance

A performance test was performed on organic electroluminescent devices provided in Application Examples 1-10 and Comparative Application Examples 1-2 as follows.

Currents were measured with Keithley 2365A digital nanovoltmeter at different voltages for the organic electroluminescent devices and then divided by a light-emitting area so that the current densities of the organic optoelectronic devices at different voltages were obtained. The brightness and radiation energy flux density of the organic electroluminescent devices manufactured according to application examples and comparative application examples at different voltages were tested with Konicaminolta CS-2000 spectrometer. According to the current densities and brightness of the organic electroluminescent devices at different voltages, an operating voltage $V_{on}$(V), a current efficiency CE (cd/A), an external quantum efficiency $EQE_{(max)}$, a color cast JNCD (30/45/60° C.) and a lifetime LT95 (which is obtained by measuring time taken for the organic electroluminescent device to reach 95% of initial brightness (under a condition of 50 mA/cm$^2$)) at the same current density (10 mA/cm$^2$) were obtained. The results are shown in Table 2.

TABLE 2

| No. | Compound | $V_{on}$ (V) | $CE_{(10\ mA/cm^2)}$ (cd A$^{-1}$) | JNCD | $EQE_{(max)}$ (%) | Lifetime LT95(h) |
|---|---|---|---|---|---|---|
| Application Example 1 | M1 | 3.52 | 6.99 | 4/2/1 | 16.5 | 67 |
| Application Example 2 | M7 | 3.51 | 7.32 | 4/3/1 | 17.1 | 72 |
| Application Example 3 | M11 | 3.46 | 7.89 | 4/2/1 | 17.3 | 70 |
| Application Example 4 | M13 | 3.41 | 7.90 | 3/2/1 | 18.1 | 69 |
| Application Example 5 | M20 | 3.46 | 7.70 | 5/2/1 | 17.2 | 68 |
| Application Example 6 | M41 | 3.45 | 7.85 | 4/3/1 | 17.9 | 69 |
| Application Example 7 | M42 | 3.46 | 8.01 | 4/2/2 | 18.5 | 67 |
| Application Example 8 | M43 | 3.45 | 7.95 | 4/3/2 | 18.2 | 71 |
| Application Example 9 | M44 | 3.45 | 8.01 | 3/2/2 | 19.1 | 70 |
| Application Example 10 | M45 | 3.44 | 7.81 | 4/3/2 | 18.2 | 73 |
| Comparative Application Example 1 | M1 | 3.46 | 7.65 | 4/3/1 | 17.6 | 68 |
| Comparative Application Example 2 | M7 | 3.51 | 7.54 | 4/2/1 | 17.2 | 67 |

It can be seen from Table 2 that when used as a material for the capping layer of the organic electroluminescent device, the compound of the present disclosure can effectively reduce the color cast of the device, improve the current efficiency and the external quantum efficiency, and provide a relatively long lifetime.

Application Example 11

This application example provides an organic electroluminescent device which has a structure shown in FIG. 2 and is prepared through specific steps described below.

(1) A glass substrate with an indium tin oxide (ITO) anode layer 2 (with a thickness of 15 nm) was cut into a size of 50 mm×50 mm×0.7 mm, sonicated in isopropyl alcohol and deionized water for 30 min separately, and cleaned under ozone for 10 min. The cleaned substrate 1 was installed onto a vacuum deposition device.

(2) A material for a hole injection layer, Compound 2, and a p-doping material, Compound 1, were co-deposited at a doping ratio of 3% (mass ratio) by means of vacuum evaporation on the ITO anode layer 2 as a hole injection layer 3 with a thickness of 5 nm.

(3) A material for a hole transport layer, Compound 2, was deposited by means of vacuum evaporation on the hole injection layer 3 as a first hole transport layer 4 with a thickness of 100 nm.

(4) A hole transport material, Compound 3, was deposited by means of vacuum evaporation on the first hole transport layer 4 as a second hole transport layer 5 with a thickness of 5 nm.

(5) A light-emitting layer 6 with a thickness of 30 nm was deposited by means of vacuum evaporation on the second hole transport layer 5, where Compound 4 was doped as a host material with Compound 5 as a doping material at a ratio of 3% (mass ratio).

(6) An electron transport material, Compound 6, was deposited by means of vacuum evaporation on the light-emitting layer 6 as a first electron transport layer 7 with a thickness of 30 nm.

(7) An electron transport material, Compound 7, and an n-doping material, Compound 8, were co-deposited at a doping mass ratio of 1:1 by means of vacuum evaporation on the first electron transport layer 7 as a second electron transport layer 8 with a thickness of 5 nm.

(8) A magnesium-silver electrode was deposited at a ratio of 9:1 by means of vacuum evaporation on the second electron transport layer 8 as a cathode 9 with a thickness of 10 nm.

(9) Compound M1 of the present disclosure was deposited by means of vacuum evaporation on the cathode 9 as a first capping layer 10 with a thickness of 100 nm.

(10) A small organic molecule D1 with a low refractive index was deposited by means of vacuum evaporation on the first capping layer 10 as a second capping layer 11 with a thickness of 20 nm.

The small organic molecules with low refractive indexes have the following structures:

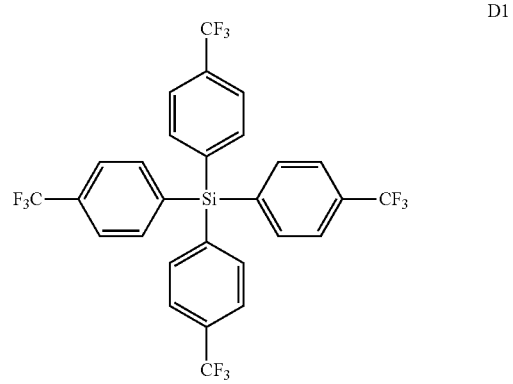

D1

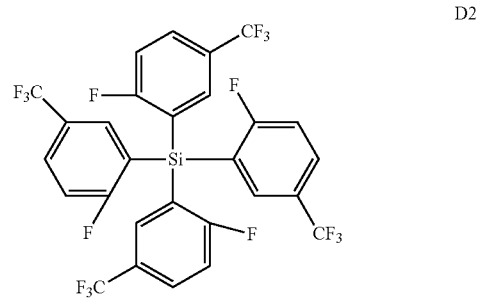

D2

-continued

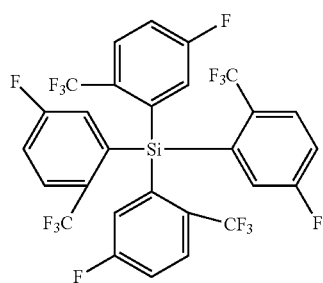

D3

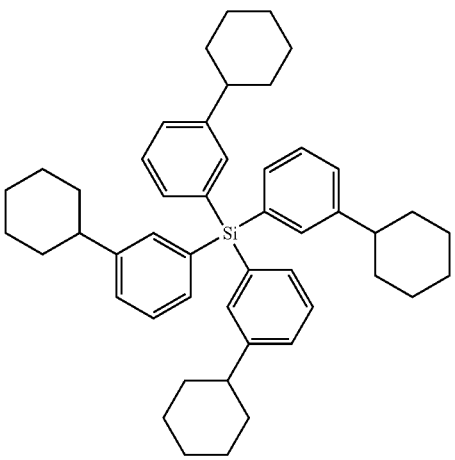

D9

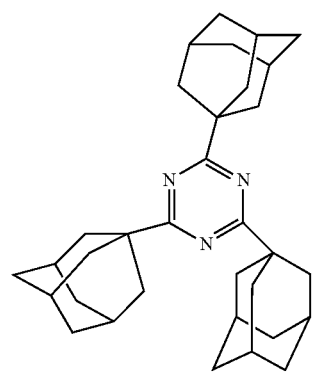

D4

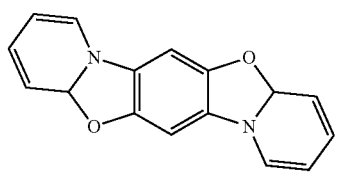

D5

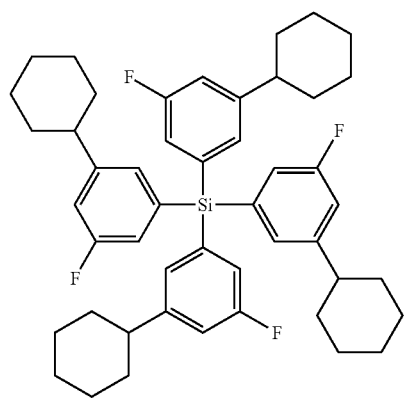

D10

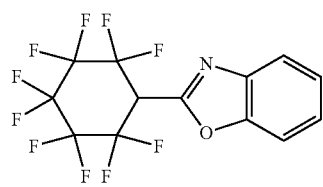

D6 and

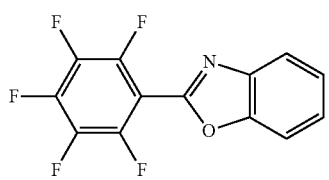

D7

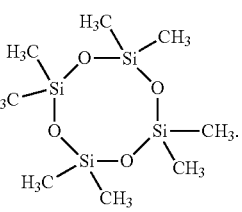

D11

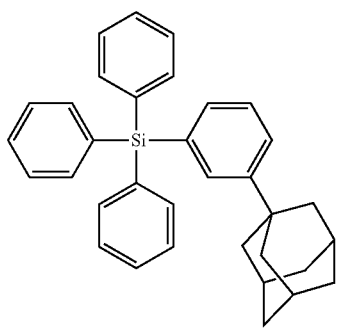

D8

Application Examples 12-21 differ from Application Example 11 only in that the small organic molecule D1 in step (10) was replaced with D2, D3, D4, D5, D6, D7, D8, D9, D10 and D11 respectively for preparing the second capping layer. All the other preparation steps are the same. Application Examples 22-24 and Comparative Application Examples 3-4 differ from Application Example 11 only in that Compound M1 in step (9) was replaced with M7, M11, M13, C1 and C2 respectively for preparing the first capping layer. For details, see Table 3.

The performance test was performed on organic electroluminescent devices provided in Application Examples 11-24 and Comparative Application Examples 3-4 by the same test method described above. The results are shown in Table 3.

TABLE 3

| No. | Material for First Capping Layer | Material for Second Capping Layer | $CE_{(10mA/cm^2)}$ (cd A$^{-1}$) | $EQE_{(max)}$ (%) |
|---|---|---|---|---|
| Application Example 11 | M1 | D1 | 7.86 | 19.2 |
| Application Example 12 | M1 | D2 | 7.88 | 19.4 |
| Application Example 13 | M1 | D3 | 7.89 | 19.6 |
| Application Example 14 | M1 | D4 | 7.86 | 19.2 |
| Application Example 15 | M1 | D5 | 7.87 | 19.1 |
| Application Example 16 | M1 | D6 | 7.87 | 19.0 |
| Application Example 17 | M1 | D7 | 7.89 | 19.5 |
| Application Example 18 | M1 | D8 | 7.87 | 19.1 |
| Application Example 19 | M1 | D9 | 7.86 | 19.0 |
| Application Example 20 | M1 | D10 | 7.96 | 19.7 |
| Application Example 21 | M1 | D11 | 8.01 | 20.1 |
| Application Example 22 | M7 | D1 | 7.92 | 19.2 |
| Application Example 23 | M11 | D1 | 7.89 | 18.9 |
| Application Example 24 | M13 | D1 | 7.89 | 18.8 |
| Comparative Application Example 3 | C1 | D1 | 6.92 | 14.9 |
| Comparative Application Example 4 | C2 | D1 | 6.93 | 14.5 |

It can be seen from Table 3 that compared with the use of Compound C1 or C2 with the material containing small organic molecules with a low refractive index used in the second capping layer, the use of the compound provided by the present disclosure as the material in the first capping layer with the material containing small organic molecules with a low refractive index used in the second capping layer is more conducive to improving the efficiency of the device, especially in terms of improving the external quantum efficiency.

What is claimed is:

1. A compound having a structure represented by Formula (1):

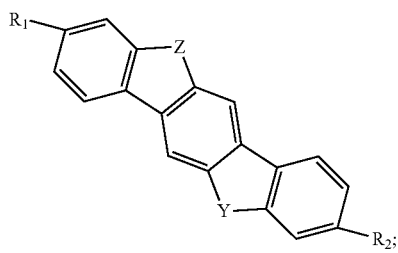

Formula (1)

wherein, $R_1$ and $R_2$ are each independently selected from the group consisting of a benzoxazole-containing group and a benzothiazole-containing group; and wherein, Y and Z are each independently selected from any one selected from the group consisting of O, S, $NR_3$ and $CR_4R_5$, wherein $R_3$ is selected from the group consisting of substituted or unsubstituted C6-C60 aryl and substituted or unsubstituted C3-C60 heteroaryl, and $R_4$ and $R_5$ are each independently any one selected from the group consisting of a hydrogen atom, substituted or unsubstituted C6-C60 aryl and substituted or unsubstituted C3-C60 heteroaryl;

wherein substituted groups in $R_3$, $R_4$ and $R_5$ are each independently any one selected from the group consisting of protium, deuterium, tritium, cyano, halogen, C1-C10 alkyl, C1-C10 haloalkyl, C1-C10 alkoxy, C6-C60 aryl, C3-C60 heteroaryl, and a combination of at least two selected therefrom.

2. The compound according to claim 1, wherein $R_1$ and $R_2$ each independently have a structure represented by Formula (2) or Formula (3):

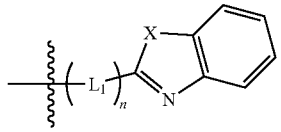

Formula (2)

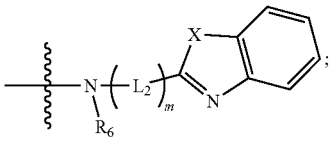

Formula (3)

wherein the squiggle represents a linkage site of the group;

wherein n and m are each independently 0 or 1, $L_1$ and $L_2$ are each independently selected from substituted or unsubstituted C6-C60 arylene, $R_6$ is selected from the group consisting of substituted or unsubstituted C6-C60 aryl and substituted or unsubstituted C3-C60 heteroaryl, and X is selected from O or S; and wherein substituted groups in $L_1$, $L_2$ and $R_6$ are each independently selected from any one selected from the group consisting of protium, deuterium, tritium, cyano, halogen, C1-C10 alkyl, C1-C10 haloalkyl, C1-C10 alkoxy, C6-C60 aryl, C3-C60 heteroaryl, and a combination of at least two selected therefrom.

3. The compound according to claim 2, wherein at least one of $R_1$ and $R_2$ has the structure represented by Formula (3).

4. The compound according to claim 2, wherein $R_1$ and $R_2$ each have the structure represented by Formula (3).

5. The compound according to claim 2, wherein n and m are each 1.

6. The compound according to claim 2, wherein $L_1$ and $L_2$ are each independently selected from substituted or unsubstituted phenylene.

7. The compound according to claim 2, wherein $R_6$ is selected from any one selected from the group consisting of substituted or unsubstituted phenyl, substituted or unsubstituted biphenyl, substituted or unsubstituted terphenyl, substituted or unsubstituted quaterphenyl, substituted or unsubstituted naphthyl, substituted or unsubstituted phenanthryl, substituted or unsubstituted fluorenyl, substituted or unsubstituted carbazolyl, substituted or unsubstituted dibenzofuryl, substituted or unsubstituted dibenzothienyl, substituted or unsubstituted pyrimidinyl, substituted or unsubstituted triazinyl, substituted or unsubstituted indolocarbazolyl, substituted or unsubstituted indolobenzofuryl, substituted or unsubstituted indolobenzothienyl, substituted or unsubstituted benzofuranpyrimidinyl, substituted or unsubstituted benzothiophenepyrimidinyl, substituted or unsubstituted anthryl, substituted or unsubstituted pyrenyl, substituted or unsubstituted pyrrolyl, substituted or unsubstituted furyl, substituted or unsubstituted thienyl, substituted or unsubstituted indolyl, substituted or unsubstituted indenocarbazolyl, substituted or unsubstituted pyridyl, substituted or unsubstituted pyrazinyl, substituted or unsubstituted pyridazinyl, and a group formed through the linkage of at least two selected therefrom.

8. The compound according to claim 2, wherein $R_6$ is selected from

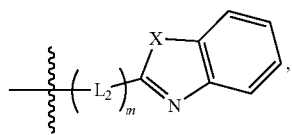

wherein $L_2$, m and X each have the same ranges as defined in Formula (3); and wherein the squiggle represents a linkage site of the group.

9. The compound according to claim 1, wherein the compound has any one of the following structures represented by M1 to M45:

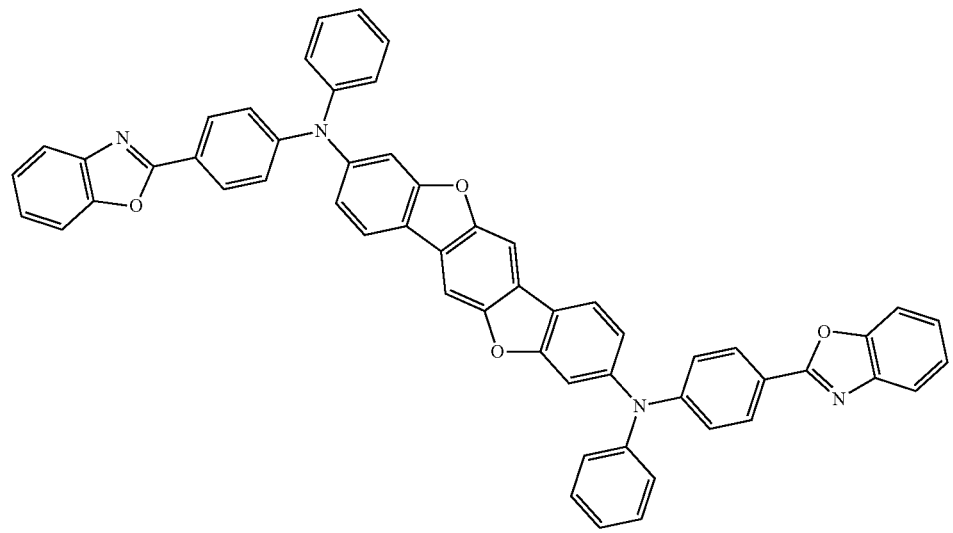

M1

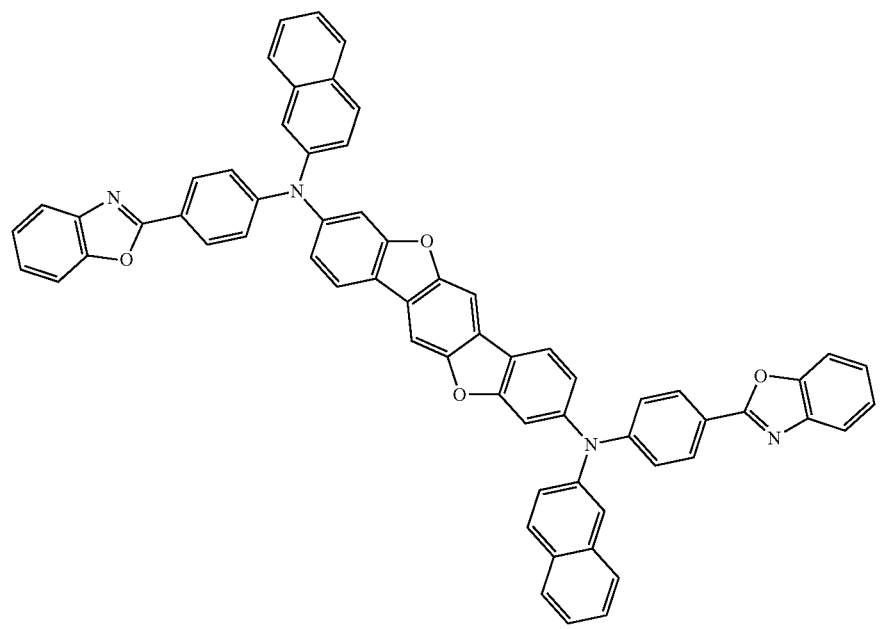

M2

-continued
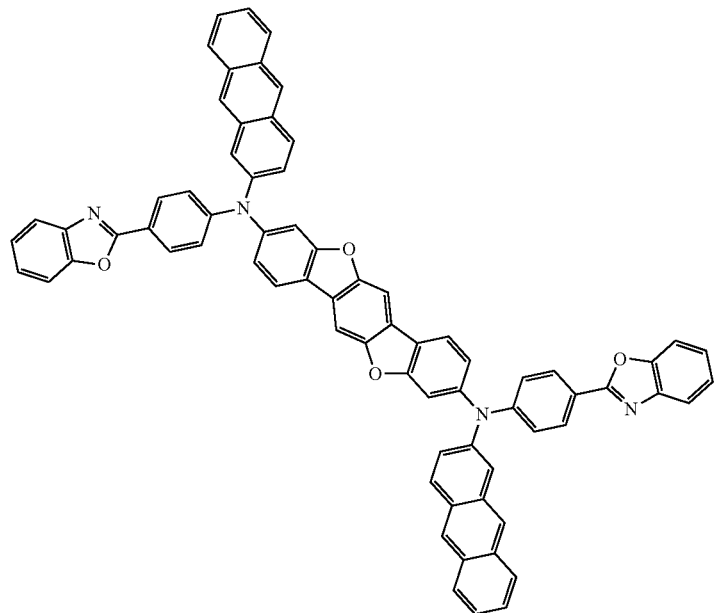
M3
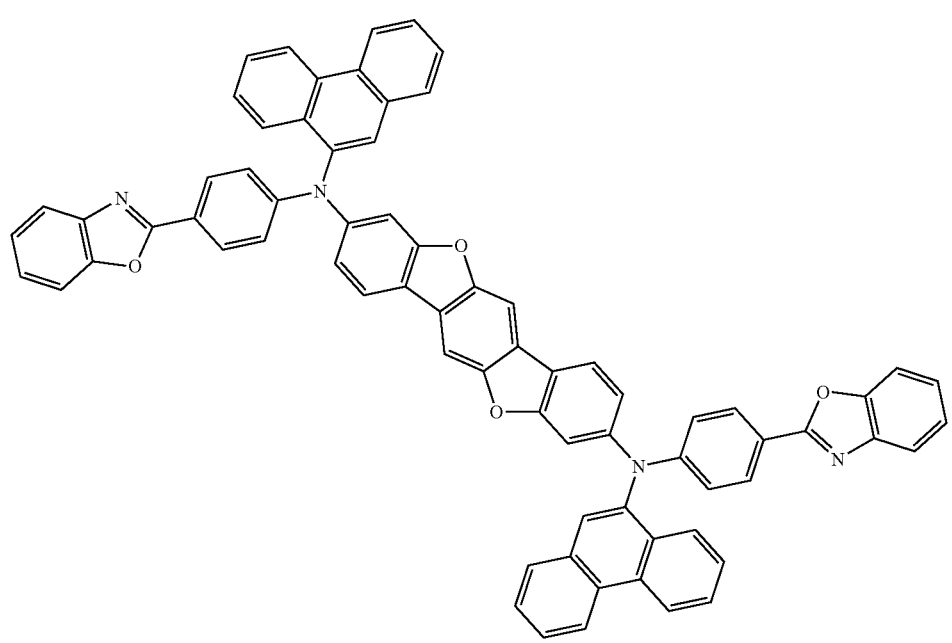
M4

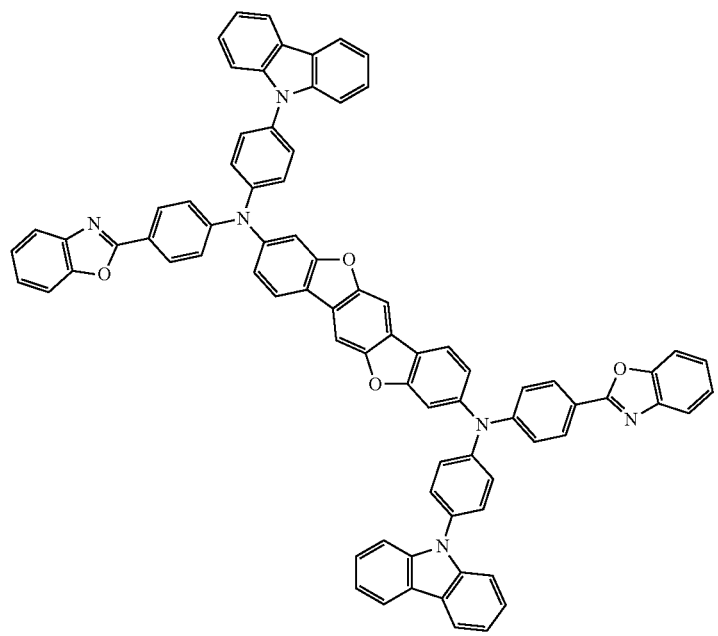
M5
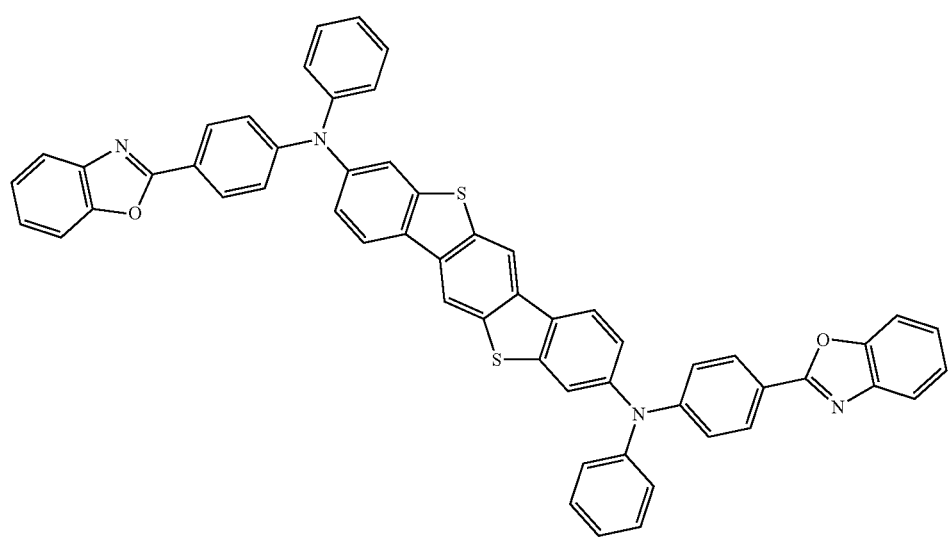
M6

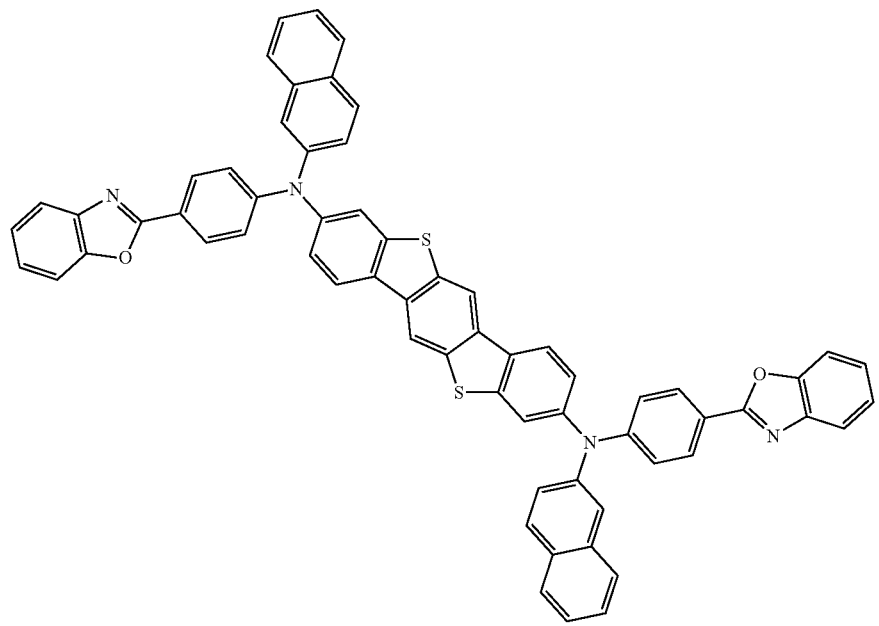
M7
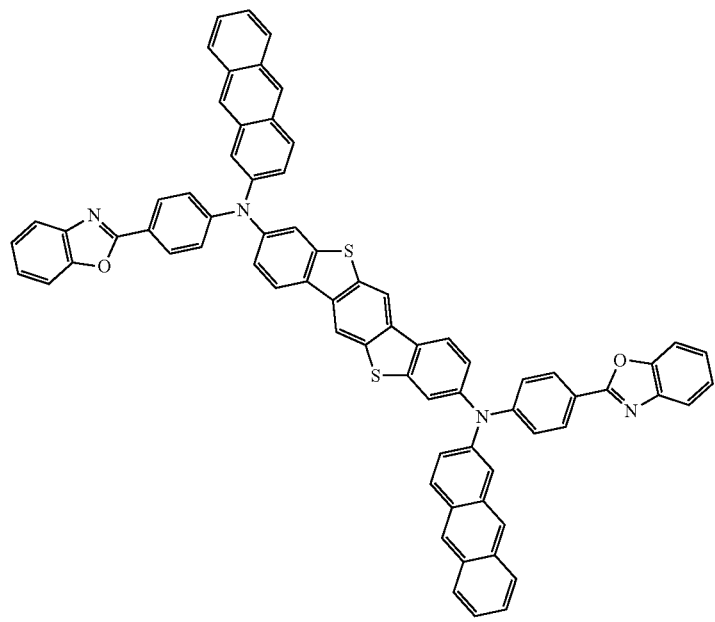
M8

-continued
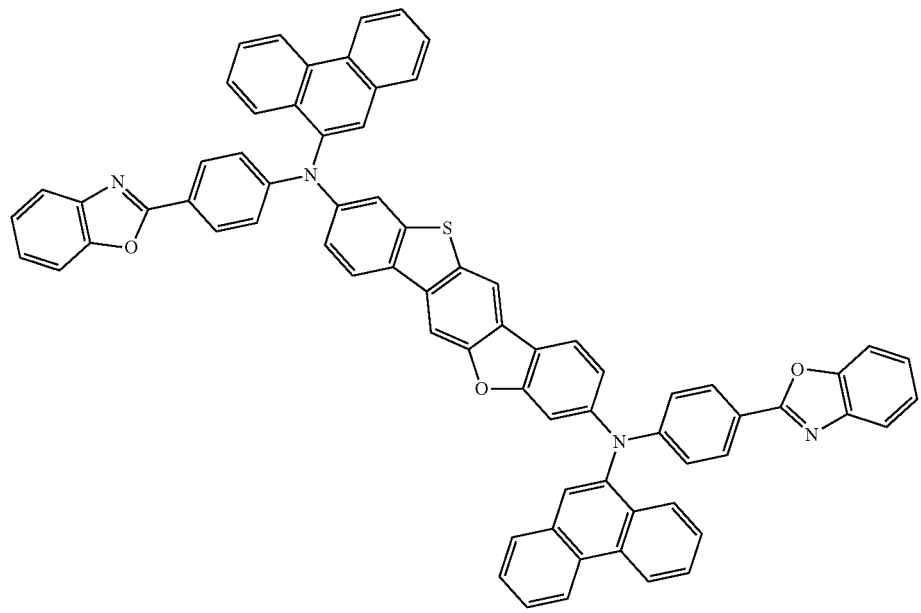
M9
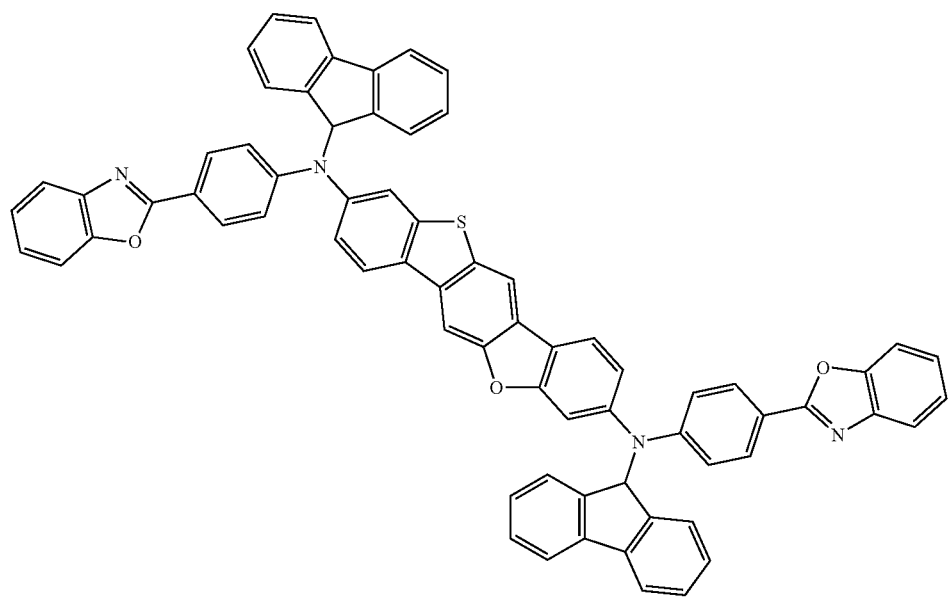
M10

M11
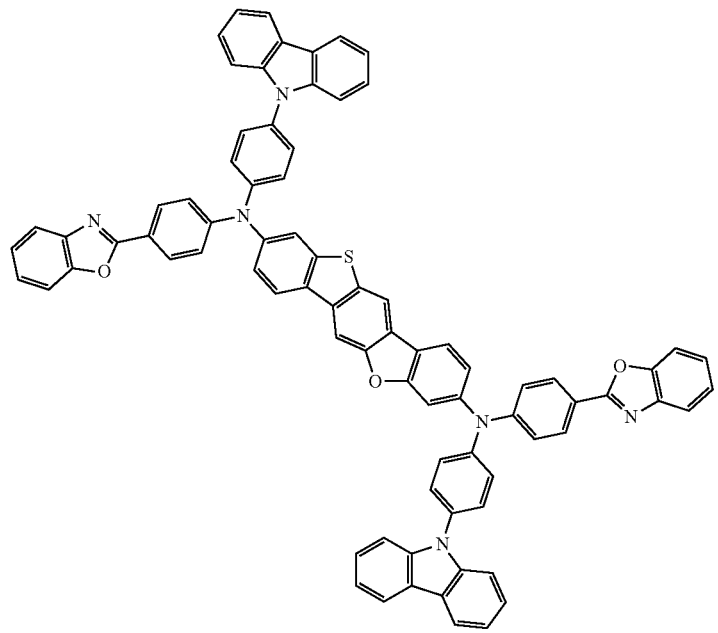
M12
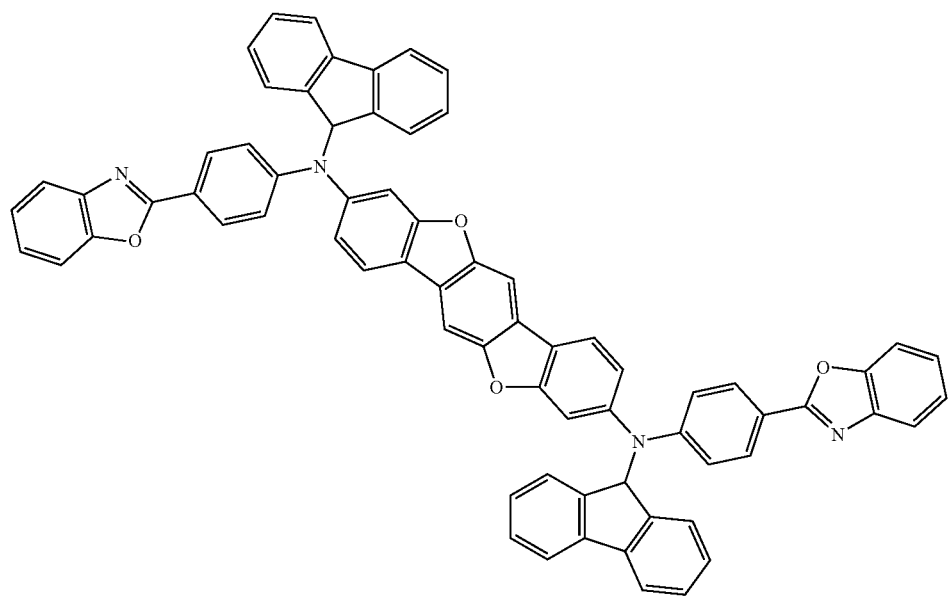
M13
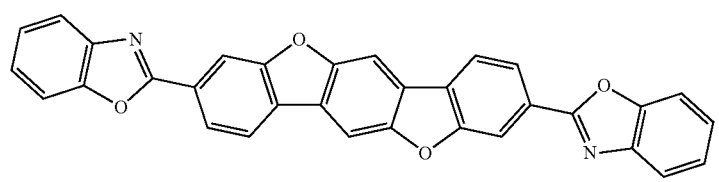

-continued
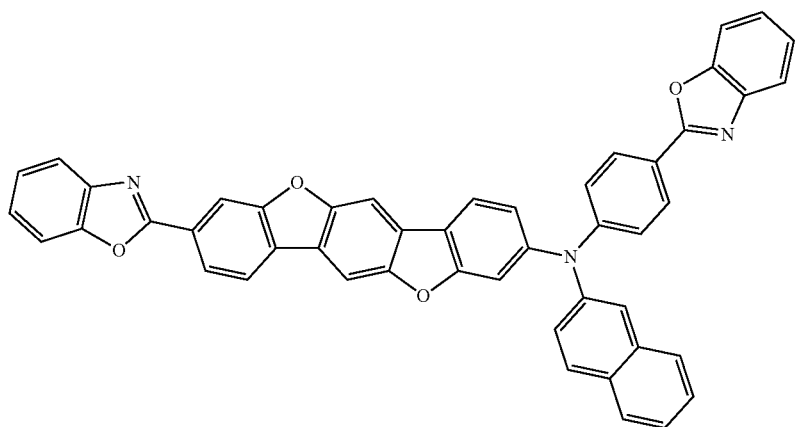
M14
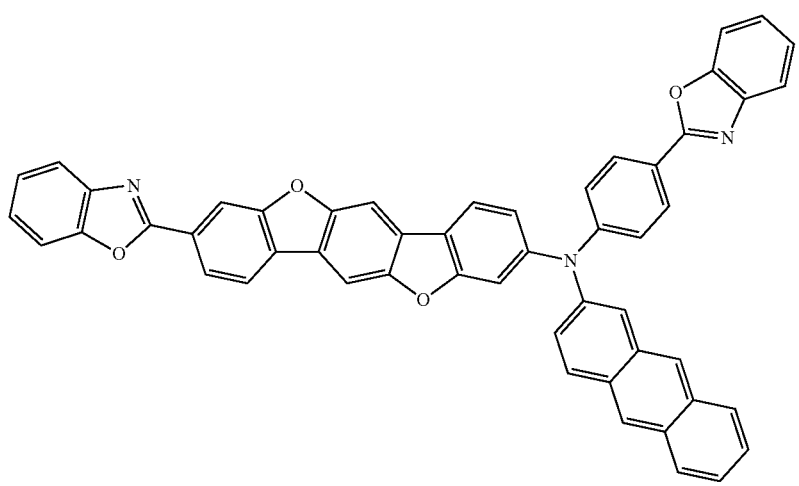
M15
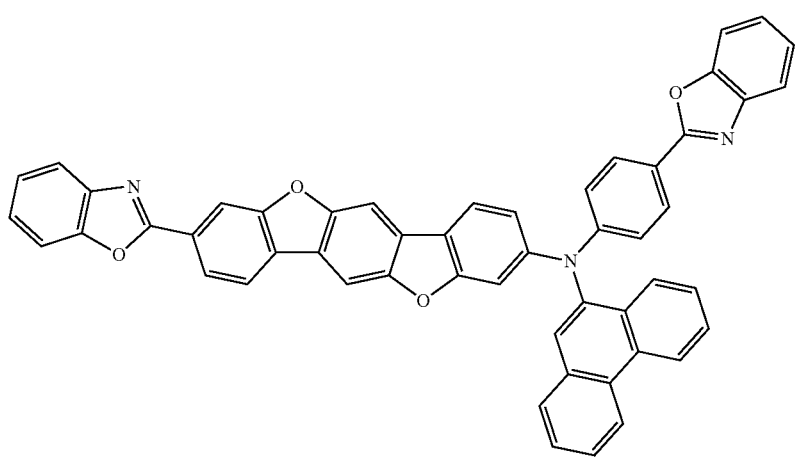
M16

M17
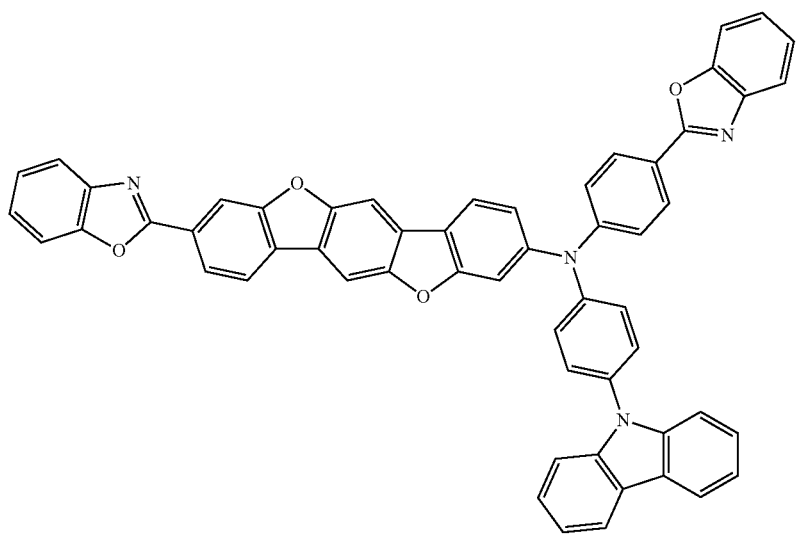
M18
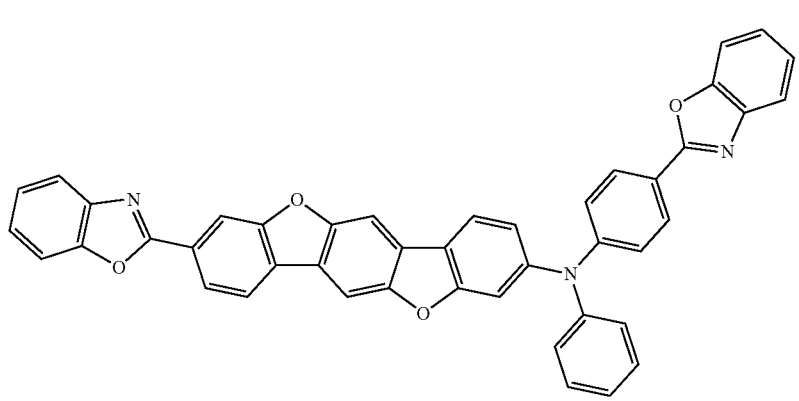
M19
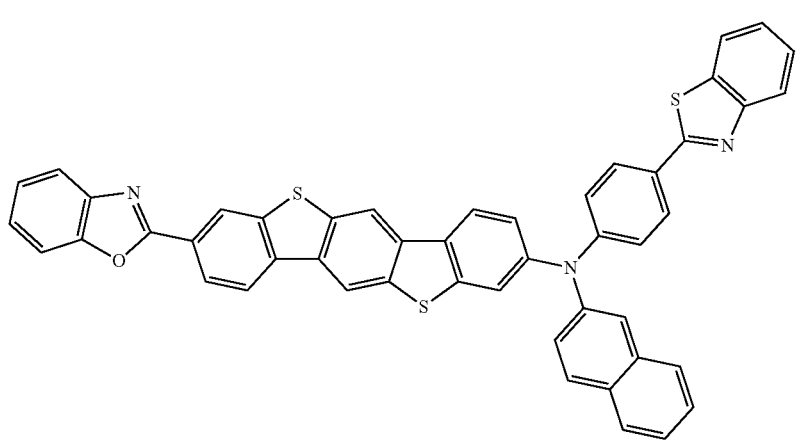

-continued
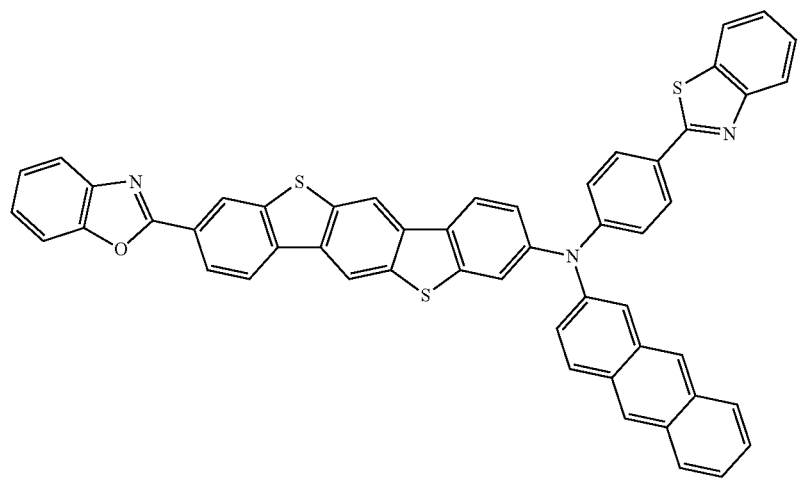
M20
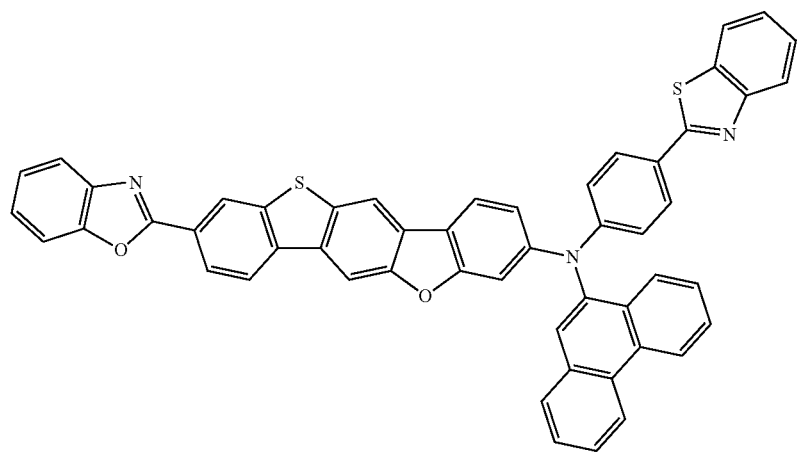
M21
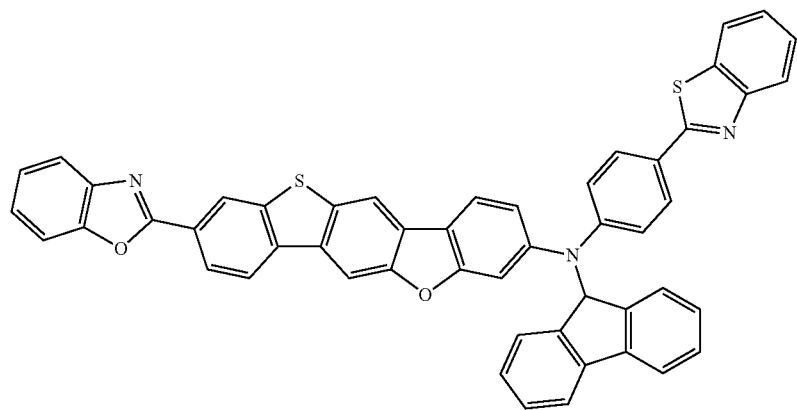
M22

M23
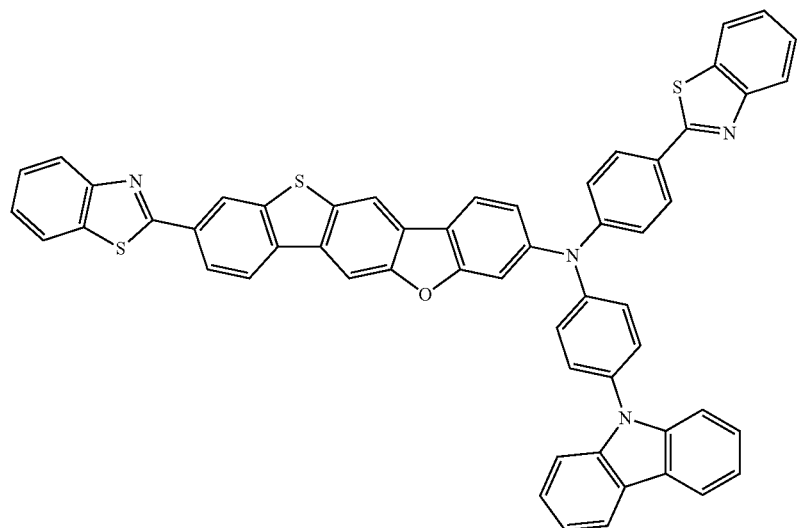
M24
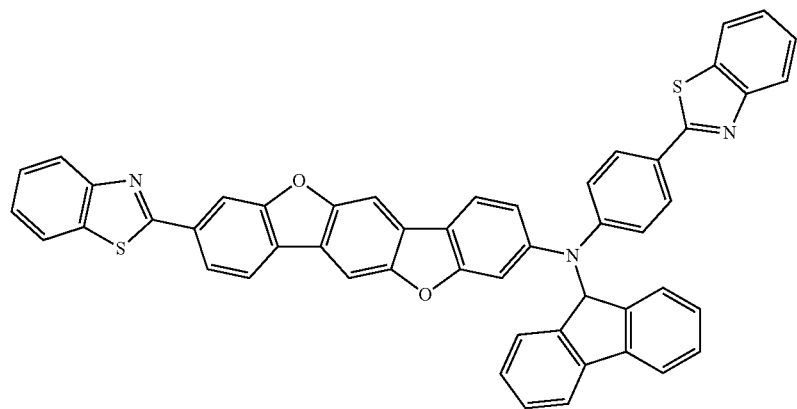
M25
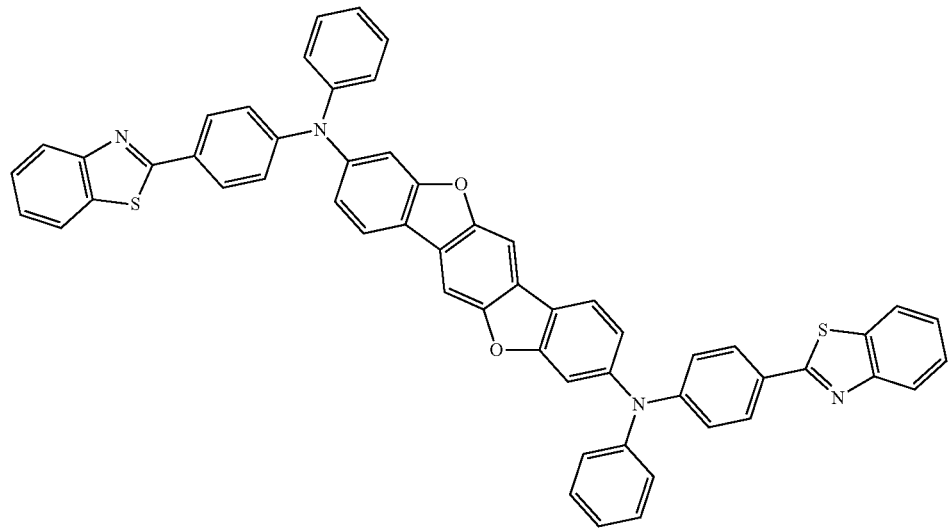

M26
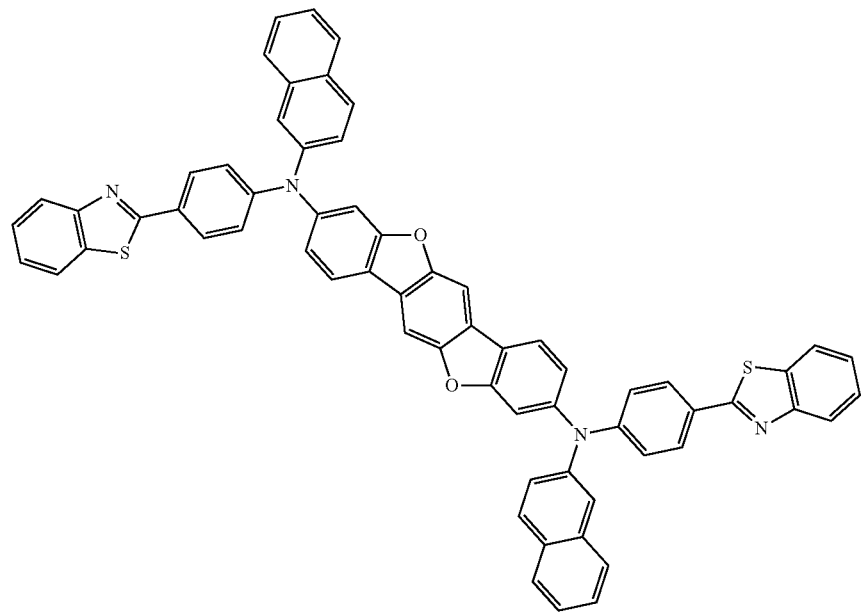
M27
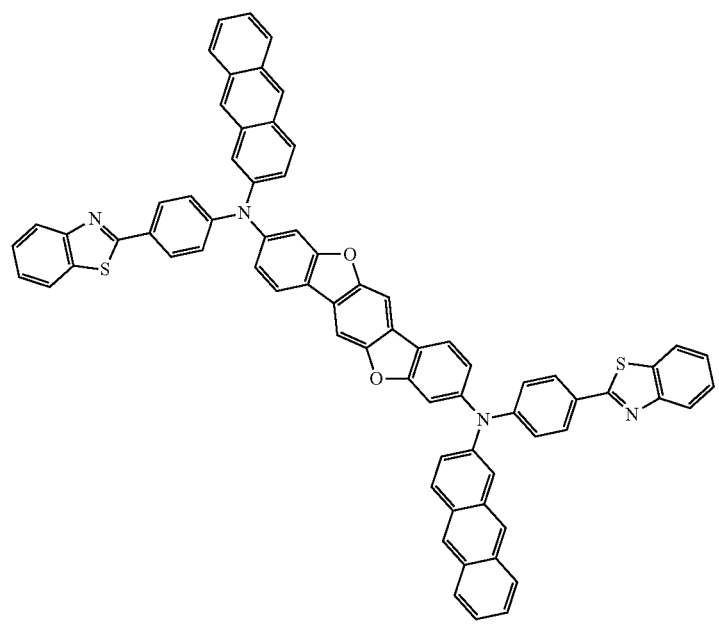

-continued
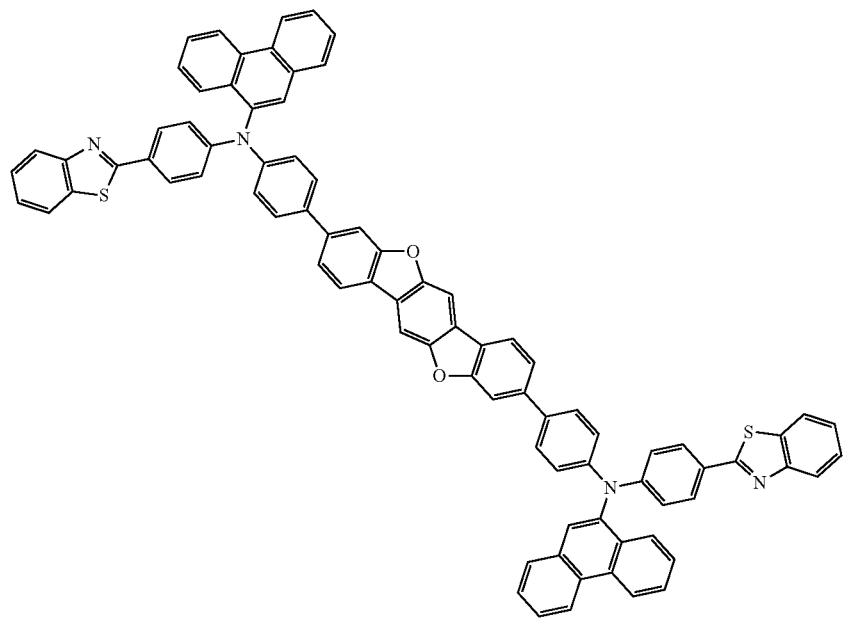
M28
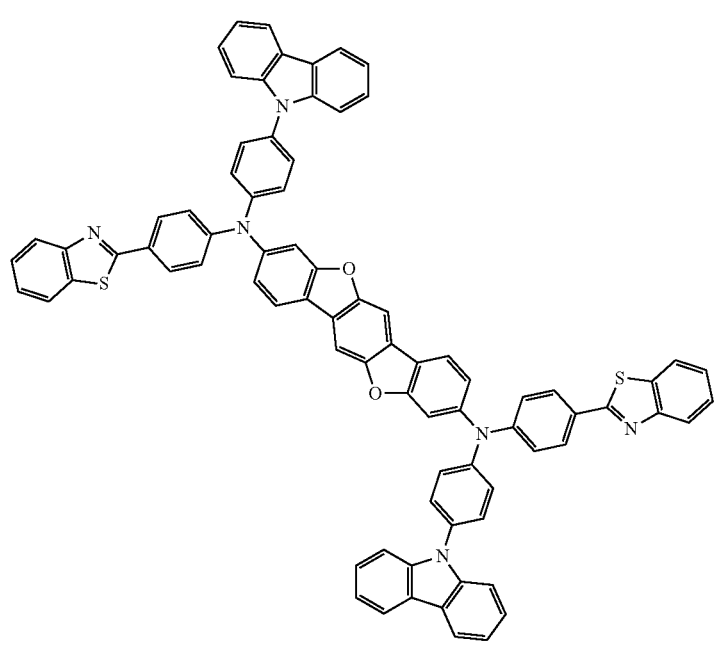
M29

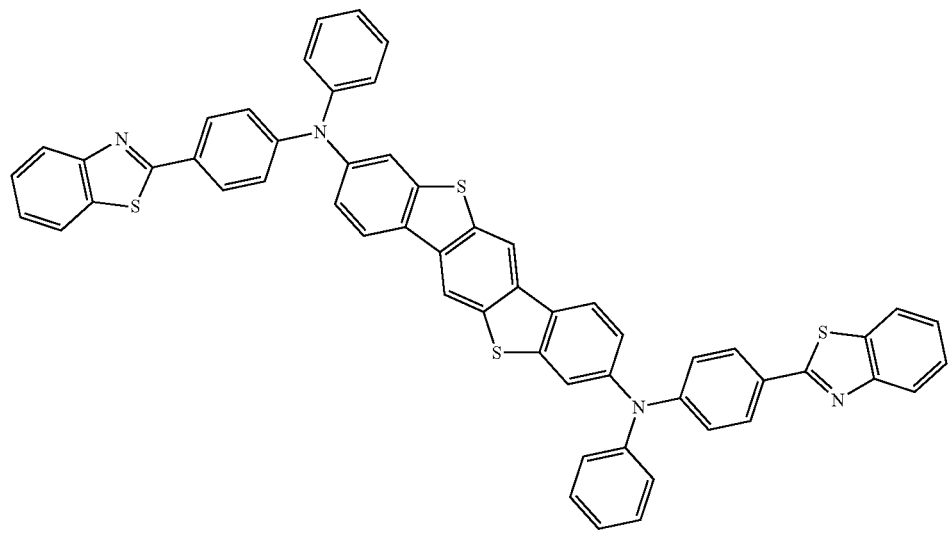
M30
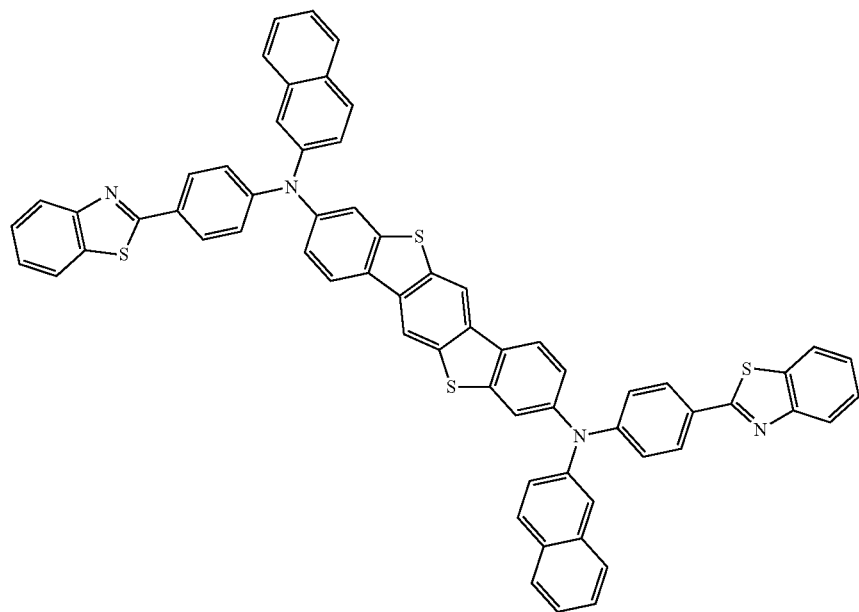
M31

-continued
M32
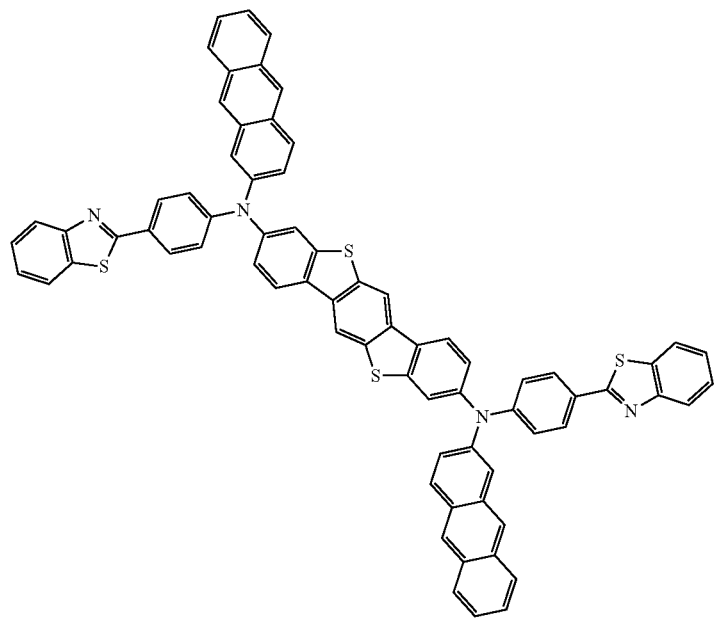
M33
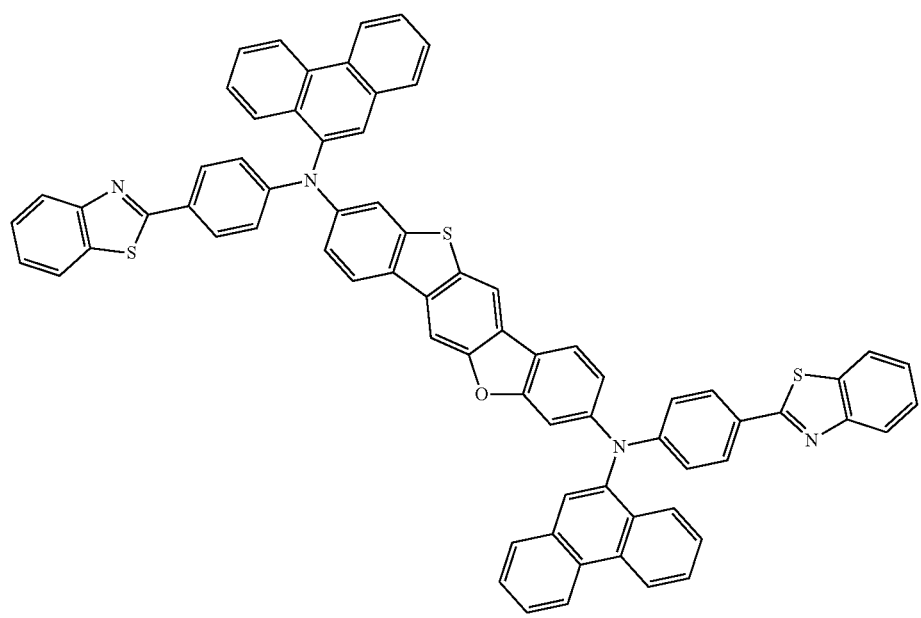

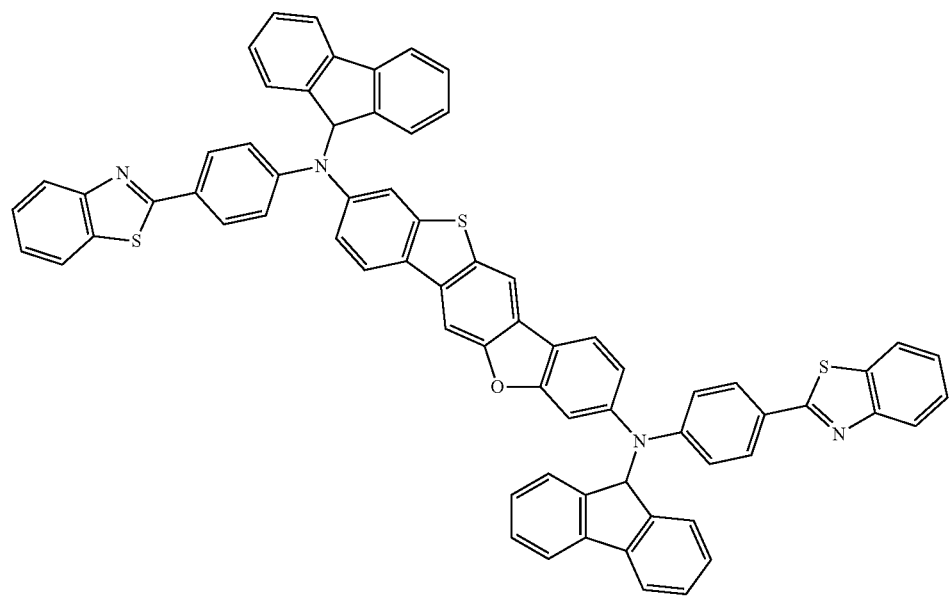
M34
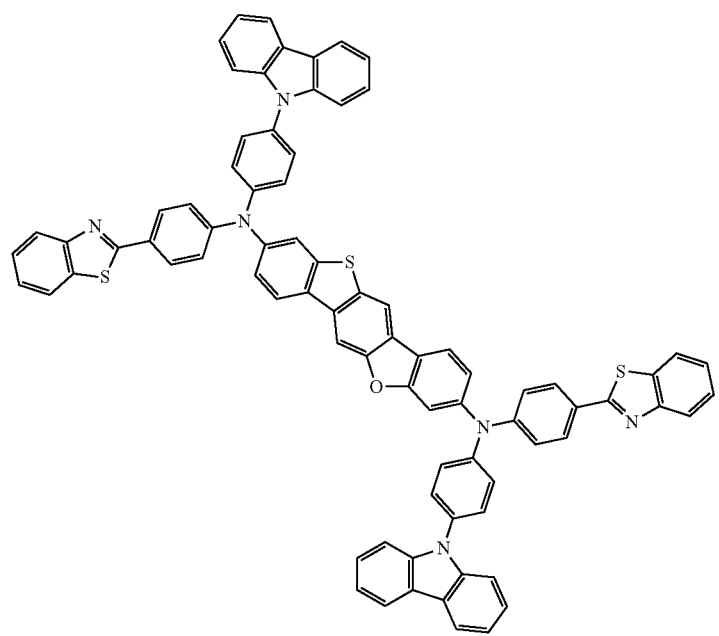
M35

M36
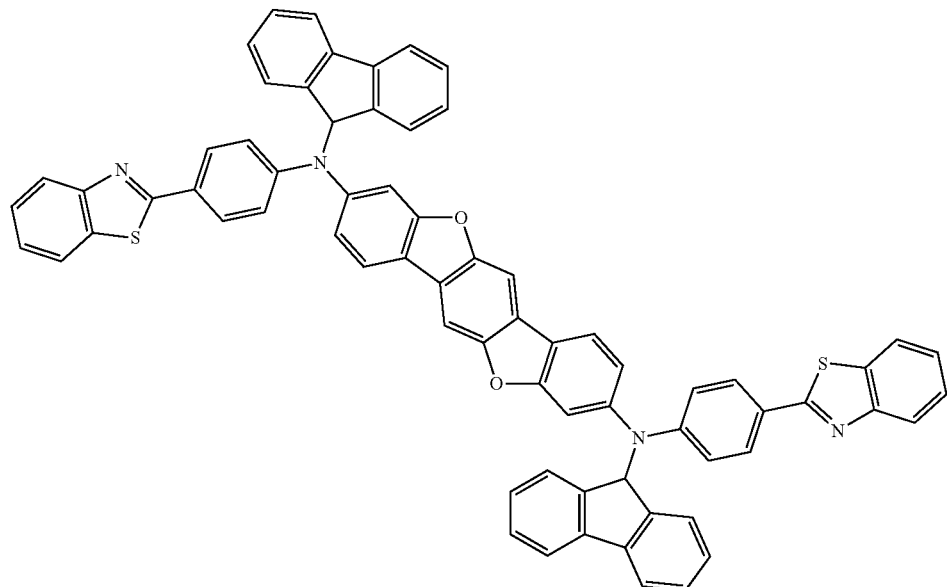
M37
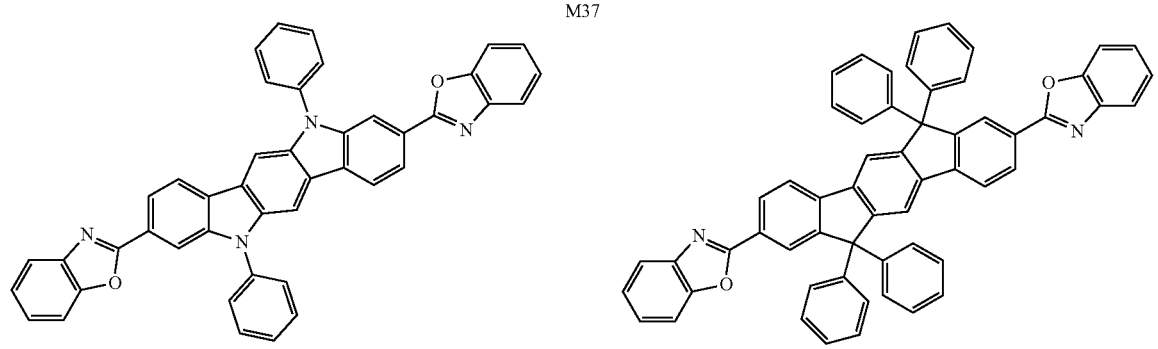
M38
M39
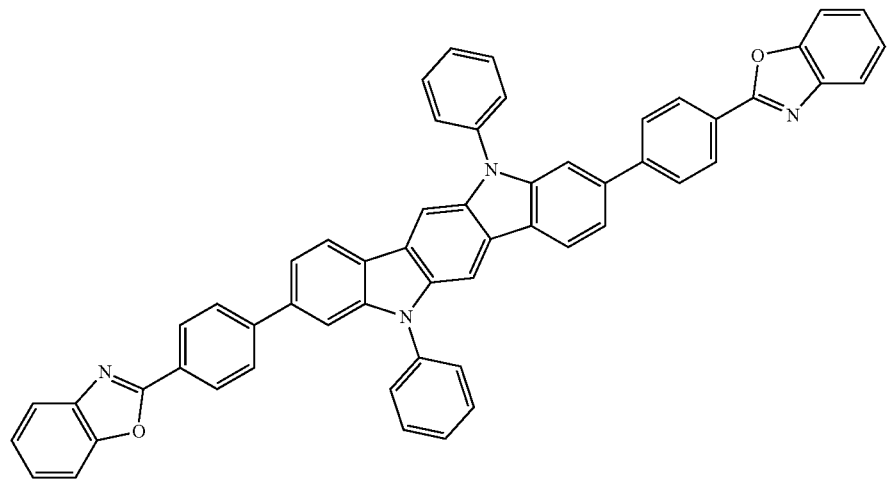

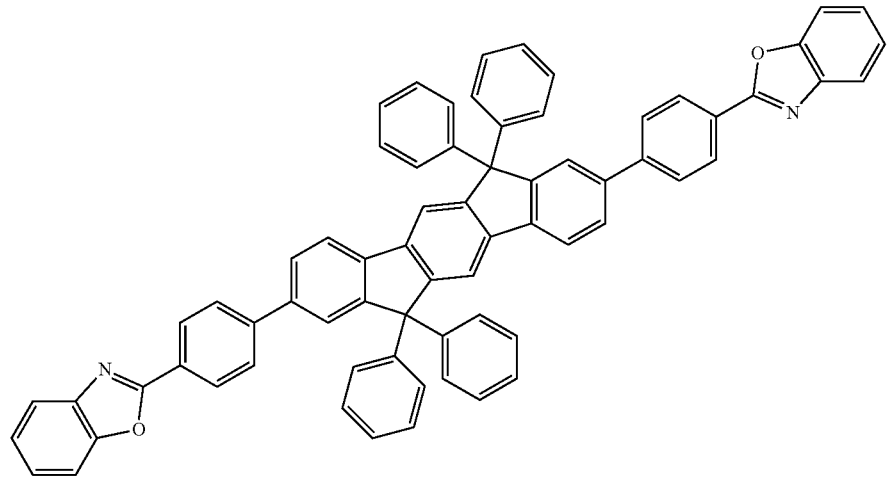
M40
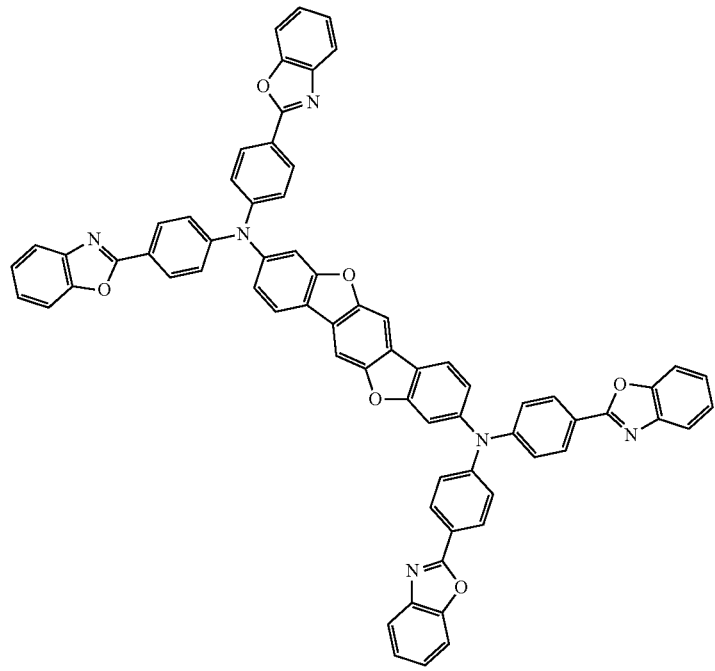
M41
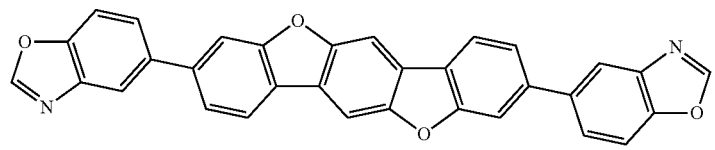
M42
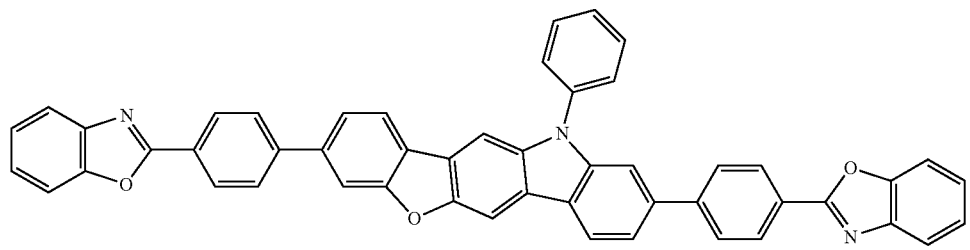
M43

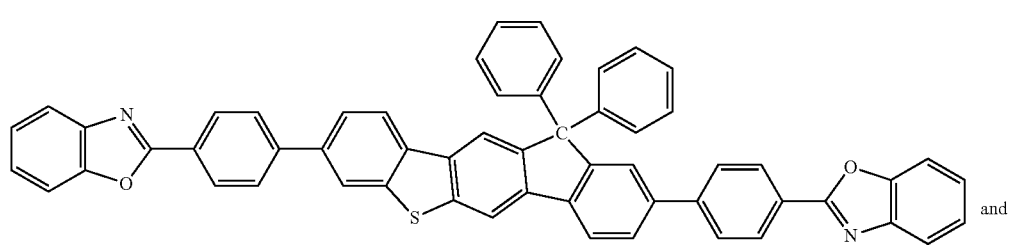 and M44

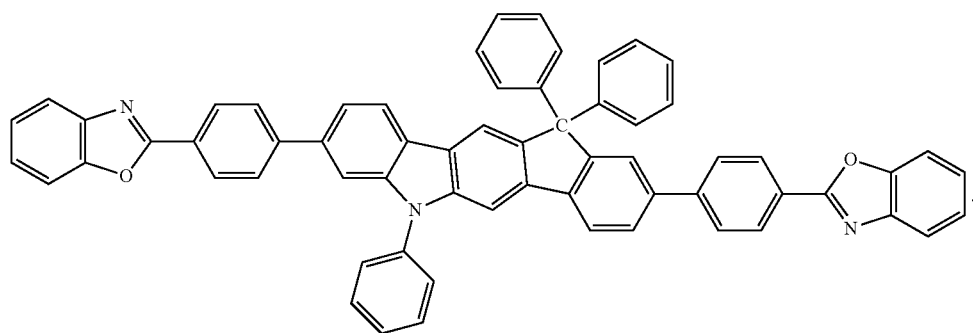 M45

10. A material for an organic electroluminescent device, comprising any one or a combination of at least two of the compound according to claim 1.

11. An organic electroluminescent element, comprising a first electrode layer, an organic function layer and a second electrode layer which are stacked in sequence;
wherein the organic function layer comprises the material according to claim 10.

12. An organic electroluminescent element, comprising a first capping layer, a first electrode layer, an organic function layer and a second electrode layer which are stacked in sequence;
wherein the first capping layer comprises the material according to claim 10.

13. The organic electroluminescent element according to claim 12, further comprising a second capping layer disposed on a side of the first capping layer facing away from the first electrode layer, wherein the second capping layer comprises lithium fluoride and/or a material containing small organic molecules with a refractive index of 1.40-1.65.

14. A display panel, comprising the organic electroluminescent element according to claim 11.

15. The display panel according to claim 14, wherein the display panel is foldable.

16. A display panel, comprising the organic electroluminescent element according to claim 12.

17. The display panel according to claim 16, wherein the display panel is foldable.

* * * * *